(12) United States Patent
Durrance et al.

(10) Patent No.: US 6,723,034 B2
(45) Date of Patent: Apr. 20, 2004

(54) PRESENTATION OF FASTENING COMPONENTS FOR MAKING PREFASTENED AND REFASTENABLE PANTS

(75) Inventors: Debra Hartley Durrance, Appleton, WI (US); Scott Gerald Chapple, Neenah, WI (US); David Michael Clemens, Menasha, WI (US); Jason Gene Csida, Reno, TX (US); Kurt Garrett Krupka, Neenah, WI (US); Heather Schenck Mortell, Neenah, WI (US); Robert Lee Popp, Hortonville, WI (US); Marcille Faye Ruman, Oshkosh, WI (US); Scott John Andrew Swanson, Neenah, WI (US); Charles Robert Tomsovic, Omro, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 6 days.

(21) Appl. No.: 09/855,451

(22) Filed: May 15, 2001

(65) Prior Publication Data

US 2002/0002358 A1 Jan. 3, 2002

Related U.S. Application Data

(60) Provisional application No. 60/204,485, filed on May 16, 2000.

(51) Int. Cl.[7] .............................................. B31B 49/00
(52) U.S. Cl. .......................... 493/373; 493/3; 493/178; 493/179; 493/357; 493/360; 493/454
(58) Field of Search ................................ 493/373, 3, 11, 493/187, 189, 381, 23, 360, 357, 425, 427, 434, 436, 437, 438, 454, 178, 179

(56) References Cited

U.S. PATENT DOCUMENTS

| 1,912,466 A | 6/1933 | Remington |
| 1,912,724 A | 6/1933 | Remington |

(List continued on next page.)

FOREIGN PATENT DOCUMENTS

| EP | 0 217 032 A2 | 4/1987 |
| EP | 0 320 989 A2 | 6/1989 |

(List continued on next page.)

*Primary Examiner*—Stephen F. Gerrity
*Assistant Examiner*—Thanh Truong
(74) *Attorney, Agent, or Firm*—Thomas M. Gage; John L. Brodersen

(57) ABSTRACT

A process for making prefastened and refastenable garments includes providing a plurality of discrete articles with mating fastening components disposed in the waist regions. First fastening components are separated from one another by an initial transverse distance. The waist region containing the first fastening components is modified to transversely displace these fastening components to a post displacement distance that is not equal to the initial distance. The process allows for convenient alignment of the fastening components to form refastenable seams.

34 Claims, 15 Drawing Sheets

U.S. PATENT DOCUMENTS

| | | | |
|---|---|---|---|
| 2,037,561 A | 4/1936 | Blosser et al. | |
| 2,714,230 A | 8/1955 | Young | |
| 3,116,920 A | 1/1964 | Geer et al. | |
| 3,502,322 A | 3/1970 | Cran | |
| 3,632,030 A | 1/1972 | Cohn et al. | |
| 3,808,767 A | 5/1974 | Reid | |
| 3,870,292 A | 3/1975 | Bradley | |
| 3,874,043 A | 4/1975 | Holm | |
| 3,913,578 A | * 10/1975 | Schaar | 604/365 |
| 3,918,706 A | 11/1975 | Craft | |
| 3,994,486 A | 11/1976 | Nystrand | |
| 4,018,432 A | 4/1977 | Frick | |
| 4,053,967 A | 10/1977 | Mair | |
| 4,145,763 A | 3/1979 | Abrams et al. | |
| 4,170,347 A | 10/1979 | Lewis | |
| 4,186,860 A | 2/1980 | Reba | |
| 4,197,621 A | 4/1980 | Mair | |
| 4,205,679 A | 6/1980 | Repke et al. | |
| 4,279,610 A | 7/1981 | Reba | |
| 4,323,534 A | 4/1982 | DesMarais | |
| 4,342,413 A | 8/1982 | Reba | |
| 4,402,690 A | 9/1983 | Redfern | |
| 4,418,513 A | 12/1983 | Plahm | |
| 4,453,709 A | 6/1984 | Reba | |
| 4,479,640 A | 10/1984 | Smith | |
| 4,516,760 A | 5/1985 | Stumpf | |
| 4,543,154 A | 9/1985 | Reiter | |
| 4,597,573 A | 7/1986 | Reba et al. | |
| 4,610,680 A | 9/1986 | LaFleur | |
| 4,615,695 A | 10/1986 | Cooper | |
| 4,640,726 A | 2/1987 | Sallee et al. | |
| 4,663,106 A | 5/1987 | Pomplun et al. | |
| 4,663,220 A | 5/1987 | Wisneski et al. | |
| 4,665,306 A | 5/1987 | Roland et al. | |
| 4,680,450 A | 7/1987 | Thorson et al. | |
| 4,698,855 A | * 10/1987 | Hicks | 2/402 |
| 4,699,622 A | 10/1987 | Toussant et al. | |
| 4,702,468 A | 10/1987 | Pollich | |
| 4,704,116 A | 11/1987 | Enloe | |
| 4,710,189 A | 12/1987 | Lash | |
| 4,717,375 A | 1/1988 | Lundmark | |
| 4,750,442 A | 6/1988 | Keeton | |
| 4,808,252 A | 2/1989 | Lash | |
| 4,834,738 A | 5/1989 | Kielpikowski et al. | |
| 4,865,579 A | 9/1989 | Kirby et al. | |
| 4,875,668 A | 10/1989 | Spyra | |
| 4,883,481 A | * 11/1989 | Blanchard | 2/402 |
| 4,883,549 A | 11/1989 | Frost et al. | |
| 4,885,853 A | 12/1989 | McCabe | |
| 4,936,840 A | 6/1990 | Proxmire | |
| 4,940,464 A | 7/1990 | Van Gompel et al. | |
| 5,046,272 A | 9/1991 | Vogt et al. | |
| 5,087,253 A | 2/1992 | Cooper | |
| 5,092,863 A | 3/1992 | Schanzlin | |
| 5,093,422 A | 3/1992 | Himes | |
| 5,104,116 A | 4/1992 | Pohjola | |
| 5,110,403 A | 5/1992 | Ehlert | |
| 5,140,757 A | 8/1992 | Terada | |
| 5,176,615 A | 1/1993 | Munsch | |
| 5,184,555 A | 2/1993 | Quadracci et al. | |
| 5,197,722 A | 3/1993 | Adamski, Jr. et al. | |
| 5,199,623 A | 4/1993 | Rajala et al. | |
| 5,224,405 A | 7/1993 | Pohjola | |
| 5,226,992 A | 7/1993 | Morman | |
| 5,300,007 A | 4/1994 | Kober | |
| 5,304,599 A | 4/1994 | Himes | |
| 5,330,598 A | 7/1994 | Erdman et al. | |
| 5,344,691 A | 9/1994 | Hanschen et al. | |
| 5,353,979 A | 10/1994 | Gartmann | |
| 5,363,784 A | 11/1994 | Adamski, Jr. et al. | |
| 5,370,634 A | 12/1994 | Ando et al. | |
| 5,399,219 A | 3/1995 | Roessler et al. | |
| 5,435,802 A | 7/1995 | Kober | |
| 5,556,360 A | 9/1996 | Kober et al. | |
| 5,626,711 A | 5/1997 | Herrmann | |
| 5,660,666 A | 8/1997 | Dilnik et al. | |
| 5,669,996 A | 9/1997 | Jessup | |
| 5,705,013 A | 1/1998 | Nease et al. | |
| 5,765,495 A | 6/1998 | Adamski, Jr. | |
| 5,766,389 A | 6/1998 | Brandon et al. | |
| 5,772,825 A | 6/1998 | Schmitz | |
| 5,779,831 A | 7/1998 | Schmitz | |
| 5,785,699 A | 7/1998 | Schmitz | |
| 5,788,805 A | 8/1998 | Herrmann | |
| 5,795,350 A | 8/1998 | Schmitz | |
| 5,795,433 A | 8/1998 | Niedermeyer | |
| 5,803,448 A | 9/1998 | Stiel et al. | |
| 5,807,368 A | 9/1998 | Helmer | |
| 5,830,206 A | 11/1998 | Larsson | |
| 5,855,574 A | 1/1999 | Kling et al. | |
| 5,858,515 A | 1/1999 | Stokes et al. | |
| 5,865,135 A | 2/1999 | Price et al. | |
| 5,897,545 A | * 4/1999 | Kline et al. | 24/304 |
| 5,904,802 A | 5/1999 | Niedermeyer | |
| 5,915,319 A | 6/1999 | Price et al. | |
| 5,916,203 A | 6/1999 | Brandon et al. | |
| 5,919,334 A | 7/1999 | Niedermeyer | |
| 5,934,470 A | * 8/1999 | Bauer et al. | 206/494 |
| 5,997,981 A | 12/1999 | McCormack et al. | |
| 6,022,431 A | 2/2000 | Blenke et al. | |
| 6,022,432 A | * 2/2000 | Elsberg et al. | 156/227 |
| 6,027,440 A | 2/2000 | Roth | |
| 6,036,805 A | 3/2000 | McNichols | |
| 6,113,717 A | 9/2000 | Vogt et al. | |
| 6,213,991 B1 | * 4/2001 | Kling et al. | 604/385.01 |
| 6,287,287 B1 | 9/2001 | Elsberg | |
| 6,328,725 B2 | 12/2001 | Fernfors | |
| 6,395,115 B1 | 5/2002 | Popp et al. | |
| 6,409,858 B1 | 6/2002 | Popp et al. | |
| 6,432,243 B1 | 8/2002 | Popp et al. | |
| 6,432,248 B1 | 8/2002 | Popp et al. | |
| 6,447,628 B1 | 9/2002 | Couillard et al. | |
| 6,461,344 B1 | 10/2002 | Widlund et al. | |
| 6,481,362 B2 | 11/2002 | Hietpas et al. | |
| 6,497,032 B2 | 12/2002 | Maxton et al. | |
| 6,513,221 B2 | 2/2003 | Vogt et al. | |
| 6,514,187 B2 | 2/2003 | Coenen et al. | |
| 6,562,167 B2 | 5/2003 | Coenen et al. | |
| 6,565,691 B2 | 5/2003 | Tomsovic et al. | |
| 6,596,113 B2 | 7/2003 | Csida et al. | |
| 2002/0173767 A1 | 11/2002 | Popp et al. | |

FOREIGN PATENT DOCUMENTS

| | | |
|---|---|---|
| EP | 0 532 486 A1 | 3/1993 |
| EP | 0 631 766 A1 | 1/1995 |
| EP | 0 689 816 A2 | 1/1996 |
| EP | 0 753 292 A2 | 1/1997 |
| EP | 0 761 193 A2 | 3/1997 |
| EP | 0 800 808 A1 | 10/1997 |
| EP | 0 803 602 A1 | 10/1997 |
| EP | 0 820 747 A1 | 1/1998 |
| EP | 0 757 550 B1 | 12/1998 |
| EP | 0 934 739 A2 | 8/1999 |
| FR | 2 299 254 | 8/1976 |
| GB | 1 384 622 | 2/1975 |
| GB | 1 520 740 | 8/1978 |
| GB | 1 593 600 | 7/1981 |
| GB | 2 160 817 A | 1/1986 |
| GB | 2 288 314 A | 10/1995 |
| WO | WO 91/19613 A1 | 12/1991 |
| WO | WO 95/18589 A1 | 7/1995 |

| WO | WO 95/18591 A2 | 7/1995 |
| WO | WO 95/27462 A1 | 10/1995 |
| WO | WO 95/32639 A1 | 12/1995 |
| WO | WO 95/33618 A1 | 12/1995 |
| WO | WO 97/23180 A1 | 7/1997 |
| WO | WO 97/24098 A1 | 7/1997 |
| WO | WO 98/15248 A1 | 4/1998 |
| WO | WO 99/65441 A1 | 12/1999 |
| WO | WO 00/23025 A1 | 4/2000 |
| WO | WO 00/35395 A2 | 6/2000 |
| WO | WO 00/35398 A1 | 6/2000 |
| WO | WO 00/37009 A2 | 6/2000 |

* cited by examiner

PRESENTATION OF FASTENING COMPONENTS FOR MAKING PREFASTENED AND REFASTENABLE PANTS

This application claims the benefit of provisional application No. 60/204,485 filed May 16, 2000.

BACKGROUND OF THE INVENTION

The present invention pertains to processes for making garments, and more particularly to processes for making refastenable garments.

Refastenable garments can include disposable absorbent garments such as diapers, training pants, absorbent swimpants, feminine care products, and incontinence products. The typical disposable absorbent garment is formed as a composite structure including an absorbent assembly disposed between a liquid permeable bodyside liner and a liquid impermeable outer cover. These components can be combined with other materials and features such as elastic materials and containment structures to form a product that is specifically suited to its intended purposes.

What is lacking and needed in the art are improved processes for making refastenable garments.

SUMMARY OF THE INVENTION

In response to the above-referenced unfulfilled need in the art, new processes for making refastenable garments have been discovered. In one aspect, the present invention relates to a process for making prefastened and refastenable pants including the steps of: providing a plurality of discrete articles, each article having first and second waist regions, a crotch region interconnecting the waist regions, first fastening components disposed in the first waist region and separated from one another by an initial distance, and second fastening components disposed in the second waist region and adapted to refastenably engage the first fastening components; transversely displacing the first fastening components so that the first fastening components are separated from one another by a post displacement distance not equal to the initial distance; and engaging the first and second fastening components subsequent to transversely displacing the first fastening components.

The first waist region can be modified to position the first fastening components closer together, that is, the post displacement distance can be less than the initial distance. The first waist region can be modified by a wide variety of methods in order to transversely displace the fastening components closer together, including but not limited to: gathering; scrunching; folding; pleating; corrugating; wrinkling; contracting; necking; contouring or shaping, such as by bowing, elevating or otherwise separating portions of the first waist region; or the like, and combinations thereof.

In one particular embodiment, the fastening components can be positioned closer together by gathering together portions of the first waist region that are disposed between the fastening components. Such gathering functions to move the fastening components closer together. The side panels can be gathered, for example, in a channel or around a bar, rod, tube, plate or the like, all of which may be uniformly shaped or contoured. Various devices can be used to gather or scrunch waist region components together to establish a modified transverse linear distance, including: a vacuum device; contoured drum; contoured roll; pressurized air nozzles; converging conveyors or chains; vertical vacuum belts; cam systems; or the like, and combinations thereof. Such devices generally modify the contour of the pant as viewed in transverse section.

The portions to be gathered can include: the absorbent chassis; the side panels, whether integral portions of the absorbent chassis or separate elements bonded to the absorbent chassis; and portions of the fastening components themselves. For example, the side panels of one waist region can be adapted to function as fastening components by refastenably engaging one or more mating fastening components disposed on the opposite waist region. Transversely inward portions of the side panels can be gathered so that transversely outward portions of the side panels are closer together.

In related embodiments, the fastening components can be positioned closer together by creating an elevation difference between portions of the first waist region containing the fastening components and another portion of the first waist region. By way of illustration, the fastening components can be disposed in the side panels, and the absorbent chassis and/or side panels can be repositioned to create an elevation difference between at least a portion of the absorbent chassis and the side panels. Creation of this elevation difference can draw the fastening components closer together in the transverse direction. The elevation difference can be created by any mechanism to displace a portion of the waist region, including a contoured roll, contoured drum, a multi-path conveyor, guiding surfaces, fluid positioning devices, or the like. Particular devices for creating an elevation distance causing fastening components to move closer together are disclosed in U.S. patent application Ser. No. 09/858,071, filed on May 15, 2001 by B. R. Vogt et al. and titled "Garment Side Panel Conveyor System And Method"; and U.S. patent application Ser. No. 09/855,450, filed on May 15, 2001 by D. A. Maxton et al. and titled "Refastenable Bonding Of Garment Side Panels"; which applications are incorporated herein by reference.

In still other embodiments, the fastening components can be positioned closer together by contracting the first waist region. The pant can comprise, for example, an activatable retractive material that is adapted to contract in a direction parallel to the transverse axis of the pant upon activation. Suitable activation methods can include without limitation any means of applying energy to the retractive material, such as heating, electromagnetic radiation such as ultraviolet, infrared, microwave, or gamma radiation; chemical modification; compaction or compression of the retractive material; or the like. Latent activation, such as inducing stretch in a material prior to applying the material to the garment and allowing the material to naturally retract over time, can also be used to transversely contract the waist region. The front and back waist regions can be constructed to contract to the same or different degrees. One waist region can be adapted to contract more than the other waist region by employing different amounts or types of materials.

The retractive material can comprise any material adapted to retract upon activation, whether immediately upon activation or subsequently thereto. The retractive material can comprise elastomeric or nonelastomeric materials. Suitable nonelastomeric retractive materials can comprise without limitation oriented films, or the like, and laminates thereof. Suitable elastomeric retractive materials can comprise without limitation LYCRA® materials, elastomeric materials including latex rubber or synthetic urethanes, or the like, and laminates thereof. In particular embodiments, the retractive material can comprise an elastomeric material having an unstable state relative to some other stable and elastic state. In such embodiments, the retractive material can but need not have elastomeric properties in the unstable state.

The first waist region can alternatively be modified to position the first fastening components farther apart, that is, the post displacement distance can be greater than the initial distance. A variety of methods can be used to transversely displace the fastening components of the first waist region farther apart, including but not limited to: altering the structure of a material; stretching a material; or the like, and combinations thereof. Various devices can be used to move the fastening components further apart, such as: a tenter frame or similar device to grab and transversely pull the first waist region; diverging conveyors such as angled vacuum conveyors; angled nip rolls; or the like, and combinations thereof.

The disclosed process can provide an efficient method of manufacturing pants with fastening components disposed on opposite surfaces. For example, in one embodiment, the present invention relates to a process for making prefastened and refastenable pants including the steps of: providing a plurality of discrete articles, each article having first and second waist regions, a crotch region interconnecting the waist regions, opposite first and second major surfaces, opposite side panels in each of the waist regions, first fastening components disposed on the first surface of the side panels in the first waist region and second fastening components disposed on the second surface of the side panels in the second waist region, the first fastening components being separated from one another by an initial distance, and the first and second fastening components adapted to refastenably engage one another; modifying the side panels in the second waist region to invert the second fastening components, the second fastening components after modification being spaced apart by a post inversion distance; transversely displacing the first fastening components so that the first fastening components are separated from one another by a post displacement distance not equal to the initial distance and substantially equal to the post inversion distance; and engaging the first and second fastening components subsequent to transversely displacing the first fastening components and inverting the second fastening components.

In particular embodiments, the first fastening components and the second fastening components can be separated from one another by substantially the same initial distance. For properly aligning the fastening components for engagement, the post displacement distance of one pair of fastening components can be substantially equal to the post inversion distance of the other pair of fastening components, whereupon the fastening components will be aligned with one another in the transverse dimension for easy engagement. In other embodiments, the initial distance between the first fastening components need not be the same as the initial distance between the second fastening components. As used herein, the terms "initial distance," "post displacement distance" and "post inversion distance" all refer to the transverse linear distance between two fastening components. The "initial" and "post" distances are measured before and after, respectively, the specified displacement or inversion. "Transverse linear distance" is used herein to refer to the distance between two fastening components, measured in a straight line parallel to the transverse axis of the garment without regard to surface contours of the garment. There may or may not be any force exerted in the transverse direction at the time of measurement.

The term "transversely displacing" as used herein refers to changing the transverse linear distance between two fastening components without inverting, that is flipping, the fastening components. Thus, modifying a waist region to change an initially-inward facing fastener to an outward direction or change an initially outward-facing fastener to an inward direction does not alone constitute transversely displacing the fastener, as that term is used herein.

Changing the transverse distance between fastening components can be useful in making a wide variety of garments. The waist regions can have the same transverse width dimensions or have different widths. Moreover, the fastening components in either waist region or in both waist regions can be transversely displaced. Accordingly, the term "first waist region" can correspond to either the front or the back waist region. Further, the fastening components in either waist region can be inverted, and in particular embodiments the fastening components in one waist region can be both transversely displaced and inverted.

The garment can be folded in half through the crotch region by a variety of mechanisms. Folding can occur before, during and/or after modification of the a waist region and/or transverse displacement of the fastening components in that waist region. Similarly, the second waist region can be modified, folded or otherwise repositioned before, during and/or after modification and/or transverse displacement of the first waist region. It may be desirable to maintain separation of the side panels and separation of the fastening components while the product is folded in half. The fastening components can be engaged simultaneously or sequentially with folding of the pant.

The fastening components can comprise separate elements bonded to another component of the pant. Alternatively, the fastening components can comprise a portion of another element of the pant, such as the bodyside liner, the outer cover, separate side panels if employed, integral side panels if employed, a belt-type component extending transversely across the chassis if employed, or the like. Thus, unless otherwise specified, the term "fastening component" includes both separate components which function as fasteners and regions of materials such as side panels, liners, outer covers or the like which function as fasteners. Moreover, a single material can define multiple fastening components to the extent that different regions of the material function as separate fasteners. The fastening components can be located on the side panels, between the side panels such as on the absorbent chassis, or a combination of the two. The fastening components can have any desired shape, such as square, rectangular, round, curved, oval, irregularly shaped, or the like. Each fastening component can comprise a single fastening element or multiple fastening elements.

The fastening components can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like. In particular embodiments, the fastening components and mating fastening components comprise hook-and-loop fastening elements. One skilled in the art will recognize that the shape, density and polymer composition of the hooks and loops may be selected to obtain the desired level of securement between the fastening components and the mating fastening components. A more aggressive hook material may comprise a material with a greater average hook height, a greater percentage of directionally-aligned hooks, or a more aggressive hook shape.

A refastenable fastening system allows for easy inspection of the interior of the pant-like product. If necessary, the fastening system also allows the pant to be removed quickly and easily. This is particularly beneficial when the pant contains messy excrement. For training pants, the caregiver can completely remove the pant-like product and replace it with a new one without having to remove the child's shoes and clothing. The refastenable fastening system may be used with a wide variety of absorbent and non-absorbent products, including training pants, swim pants, diaper pants, incontinence garments, feminine care products, health care garments, apparel for institutional, industrial and consumer use, or other garments using mechanical or adhesive fasteners.

Absorbent articles are adapted to be worn adjacent to the body of a wearer to absorb and contain various exudates discharged from the body. The absorbent articles are desirably prefastened to provide a pant-like product for the user. The product can then be pulled on like a conventional training pant, and subsequently checked or removed with the ease of a diaper-like product. Moreover, the product may be applied like a diaper rather than like a pant. Supplemental releasable fastening means such as frangible point bonds may be employed to maintain the absorbent article in a pant configuration until the user intentionally disengages the fasteners.

Particular training pants suitable for use with the present invention are disclosed in U. S. patent application Ser. No. 09/444,083, filed on Nov. 22, 1999 (corresponding to PCT application WO 00/37009 published Jun. 29, 2000) by A. Fletcher et al. and titled "Absorbent Articles With Refastenable Side Seams;" which is incorporated herein by reference. This reference describes various materials and methods for constructing training pants. Training pants can also be constructed using the methods and apparatus disclosed in U.S. Pat. No. 4,940,464 issued Jul. 10, 1990 to Van Gompel et al.; and U.S. Pat. No. 5,766,389 issued Jun. 16, 1998 to Brandon et al.; which are also incorporated herein by reference.

Definitions

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The methods and apparatus of the present invention can be used to make a variety of garments. Examples of such garments include disposable absorbent articles such as diapers, training pants, feminine hygiene products, incontinence products, other personal care or health care garments; swim pants; athletic clothing; pants and shorts; or the like. For ease of explanation, the description hereafter will be in terms of methods and apparatus for making a child's training pant. In particular, the methods and apparatus will be described in terms of those for making prefastened disposable training pants as described in U.S. patent application Ser. No. 09/444,083 titled "Absorbent Articles With Refastenable Side Seams" and filed Nov. 22, 1999 by A. L. Fletcher et al. (corresponding to PCT application WO 00/37009 published Jun. 29, 2000), the disclosure of which is incorporated herein by reference.

Figure 1:
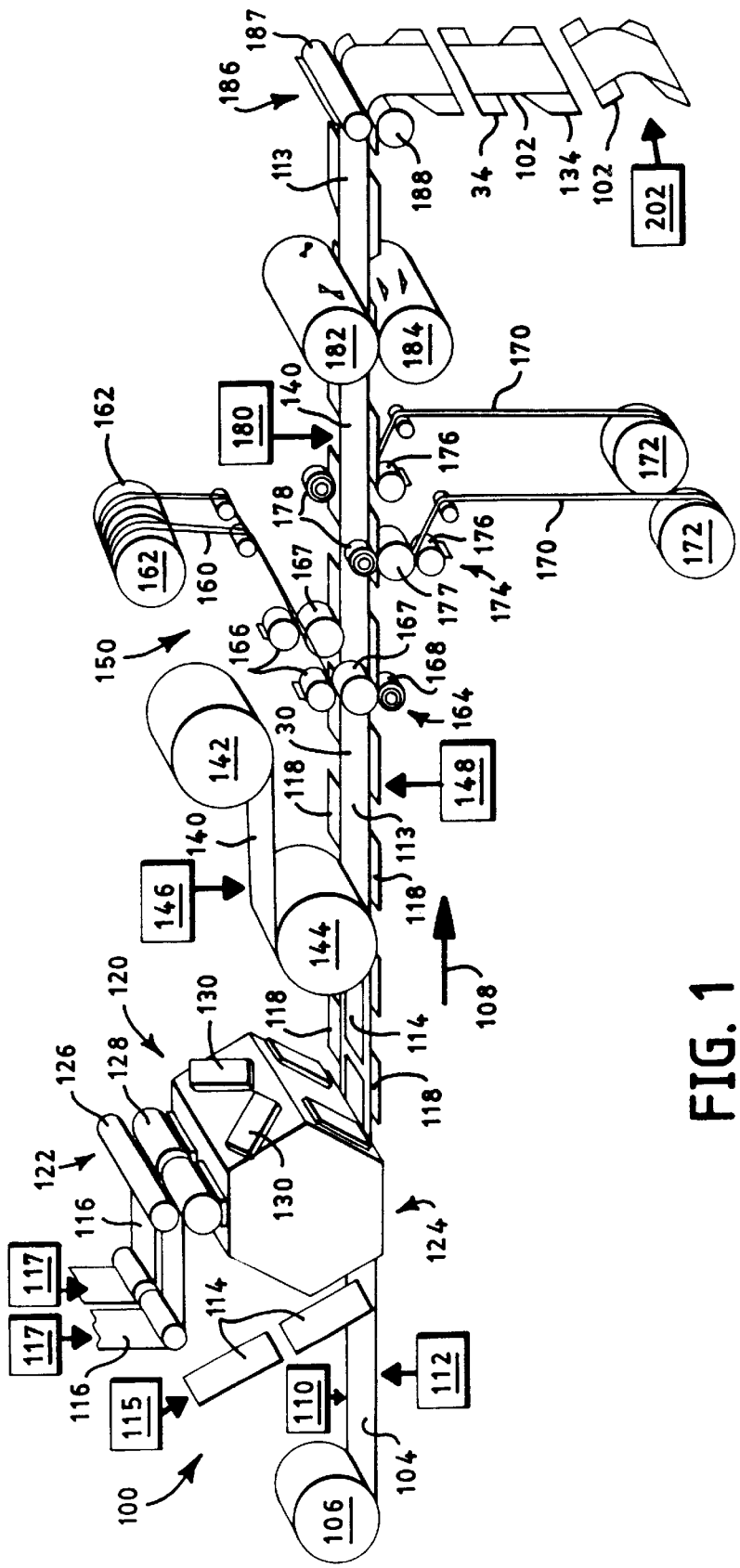
FIG. 1 is a schematic view of an exemplary embodiment of an assembly section for making garments such as training pants.
Figure 2:
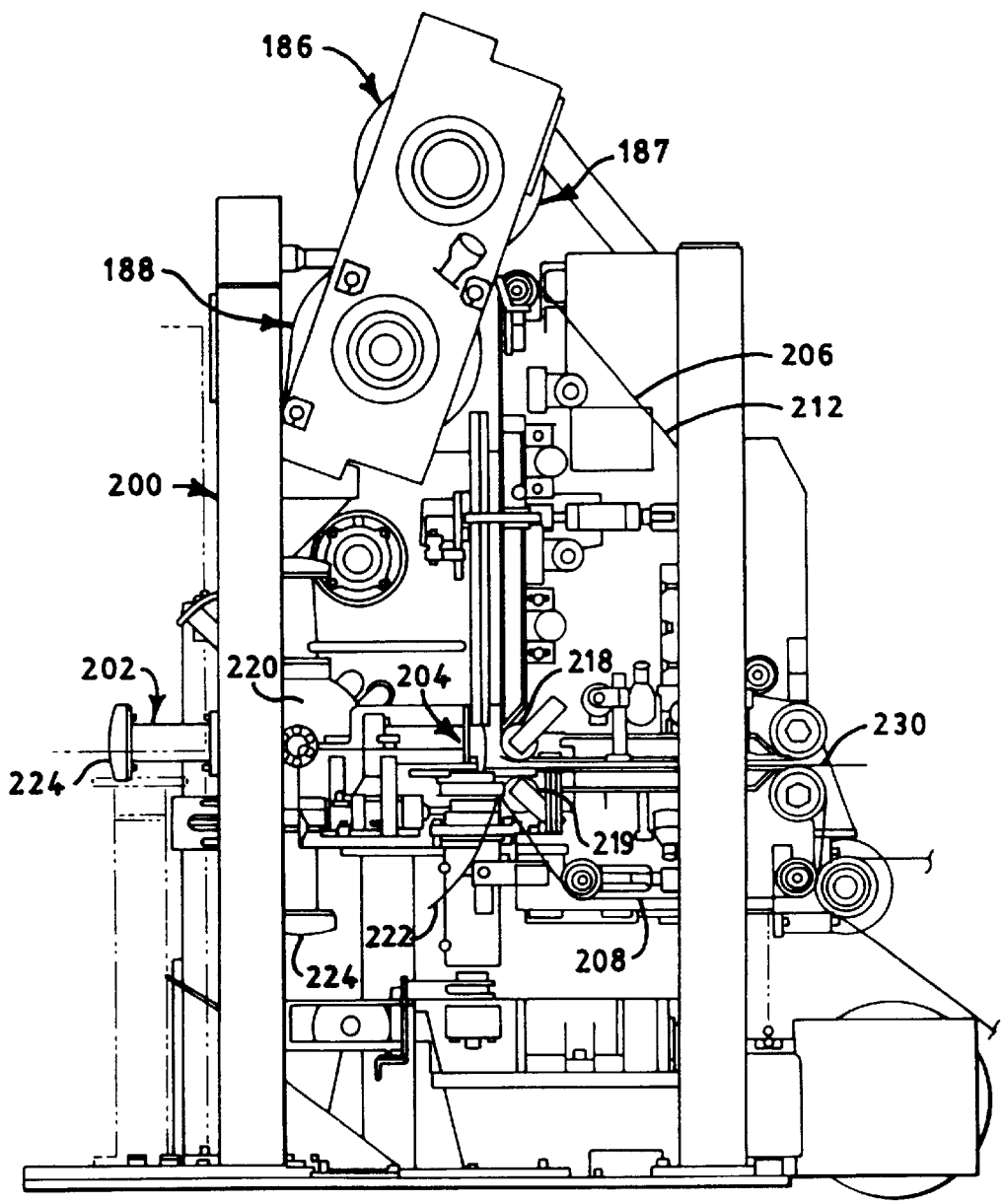
FIG. 2 is a schematic side view of an exemplary embodiment of a folding section for making garments such as training pants, the folding section following the assembly section shown in FIG. 1.
Figure 3:
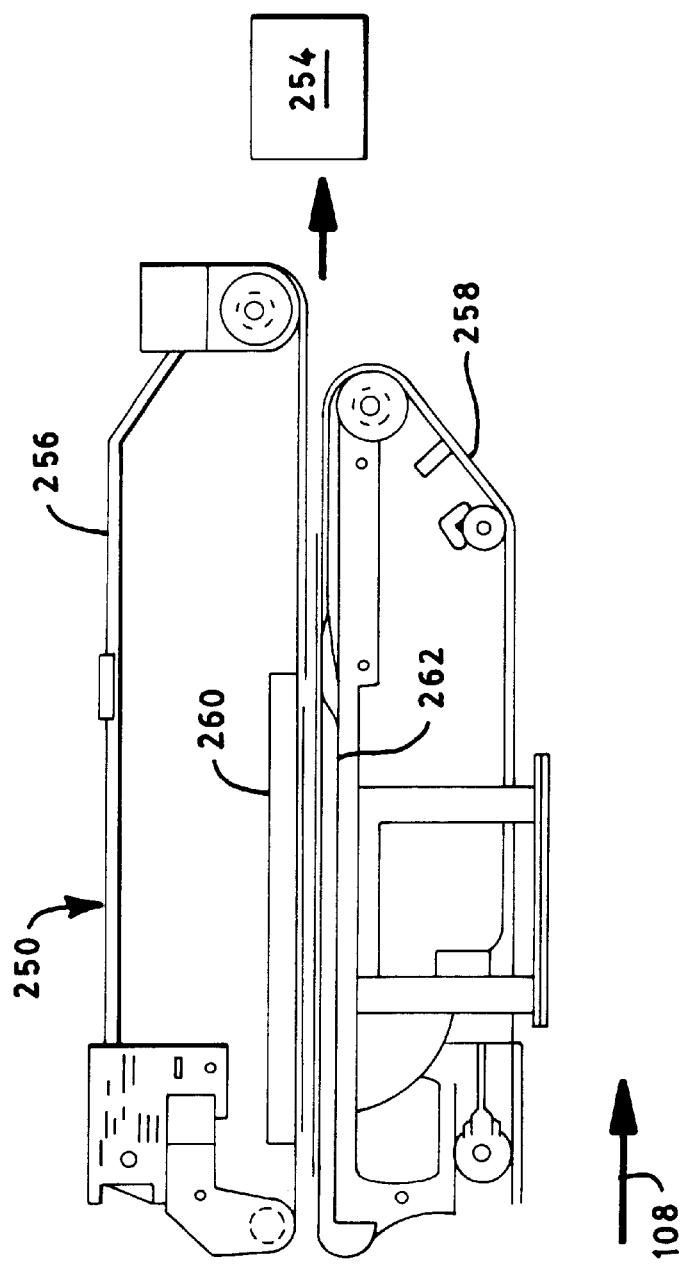
FIG. 3 is a schematic side view of one embodiment of a method and apparatus for making garments according to the present invention, the view illustrating a seaming section which follows the folding section shown in FIG. 2.

FIGS. 1–3 representatively illustrate one embodiment of a method and apparatus for making a training pant 20. The training pant 20 is illustrated separately and in a partially fastened condition in FIG. 4. The training pant 20 comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 5 and 6, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

Figure 4:
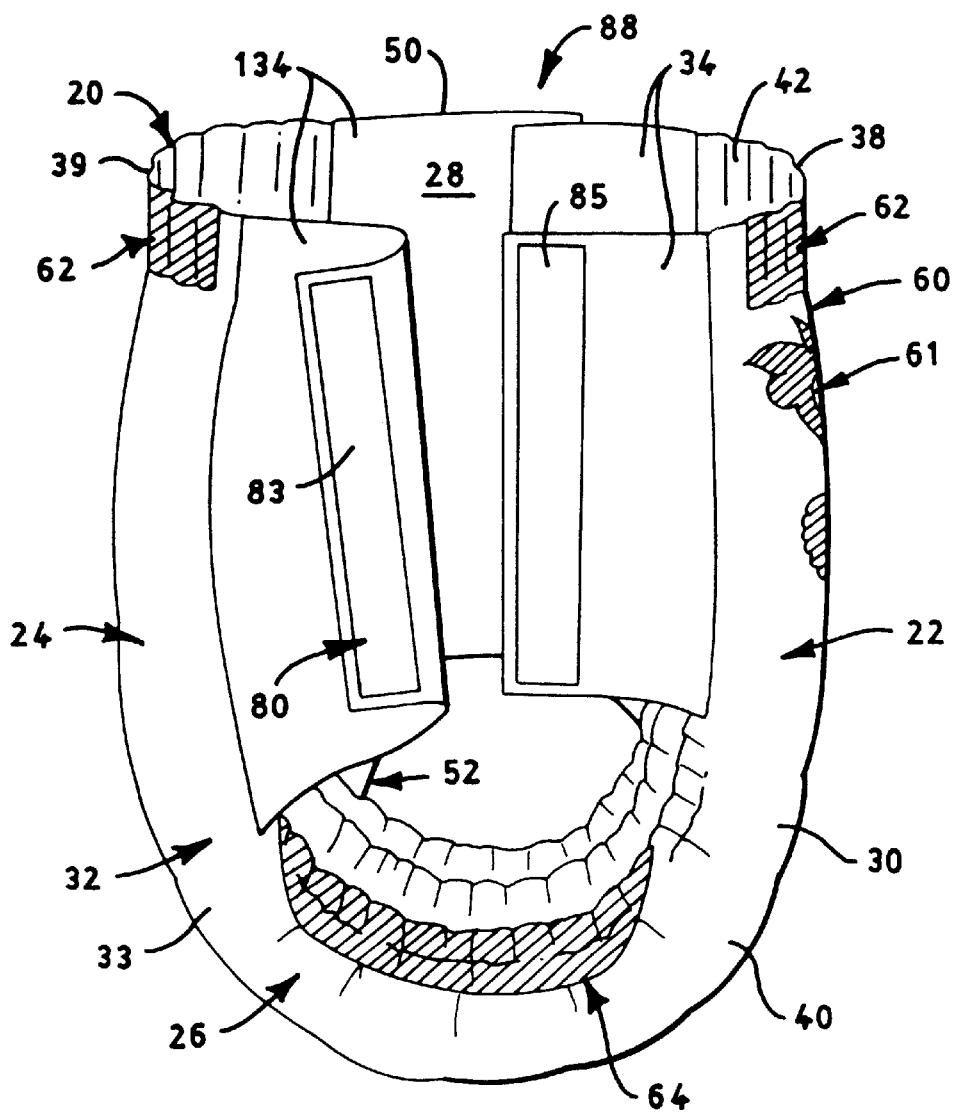
FIG. 4 illustrates a side view of a training pant made by the process and apparatus shown in FIGS. 1–3, where the fastening system is shown engaged on one side of the training pant and disengaged on the other side of the training pant.
Figure 5:
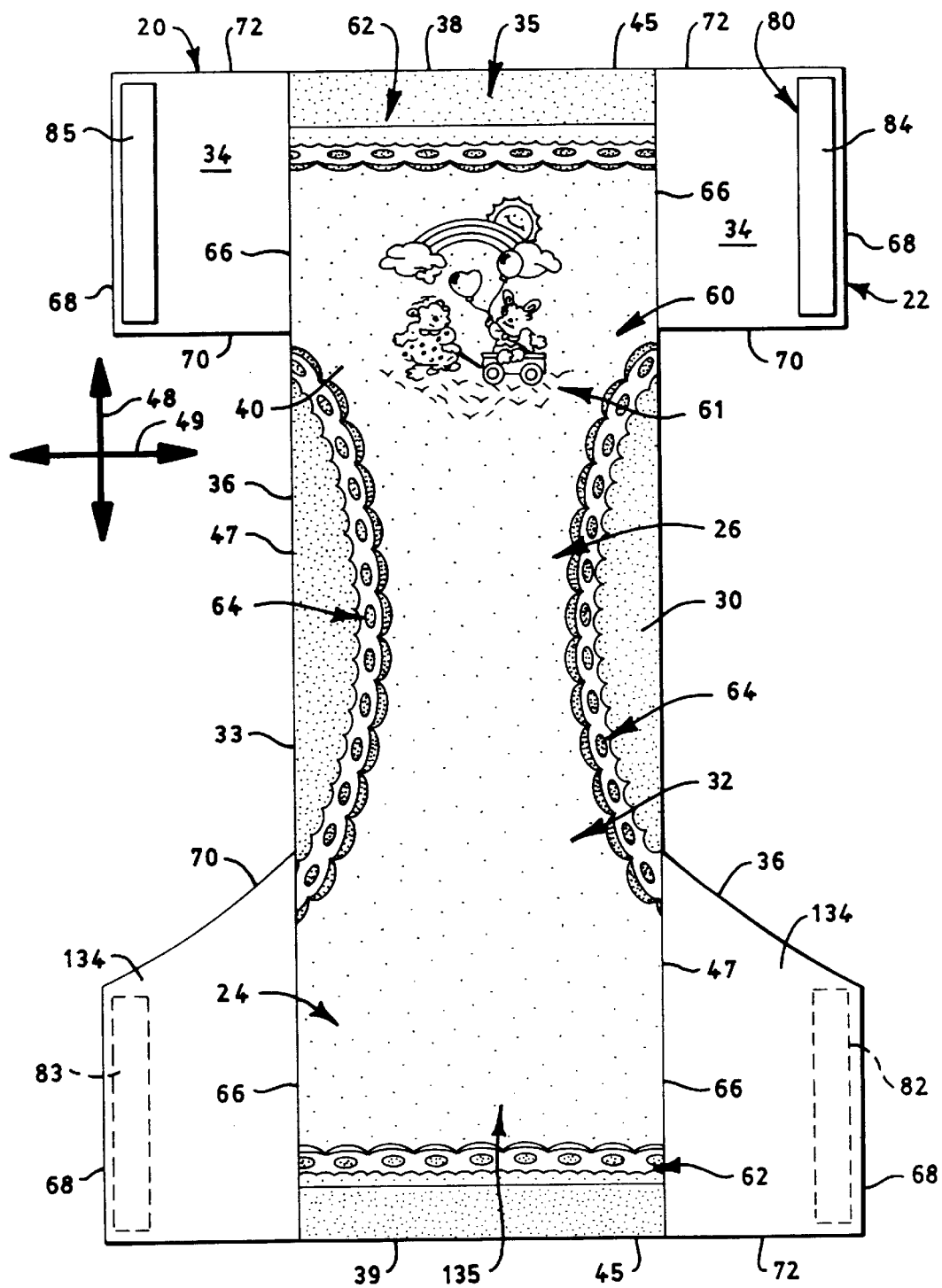
FIG. 5 illustrates a plan view of the training pant shown in FIG. 4 in an unfastened, stretched and laid flat condition, and showing the surface of the training pant that faces away from the wearer.
Figure 6:
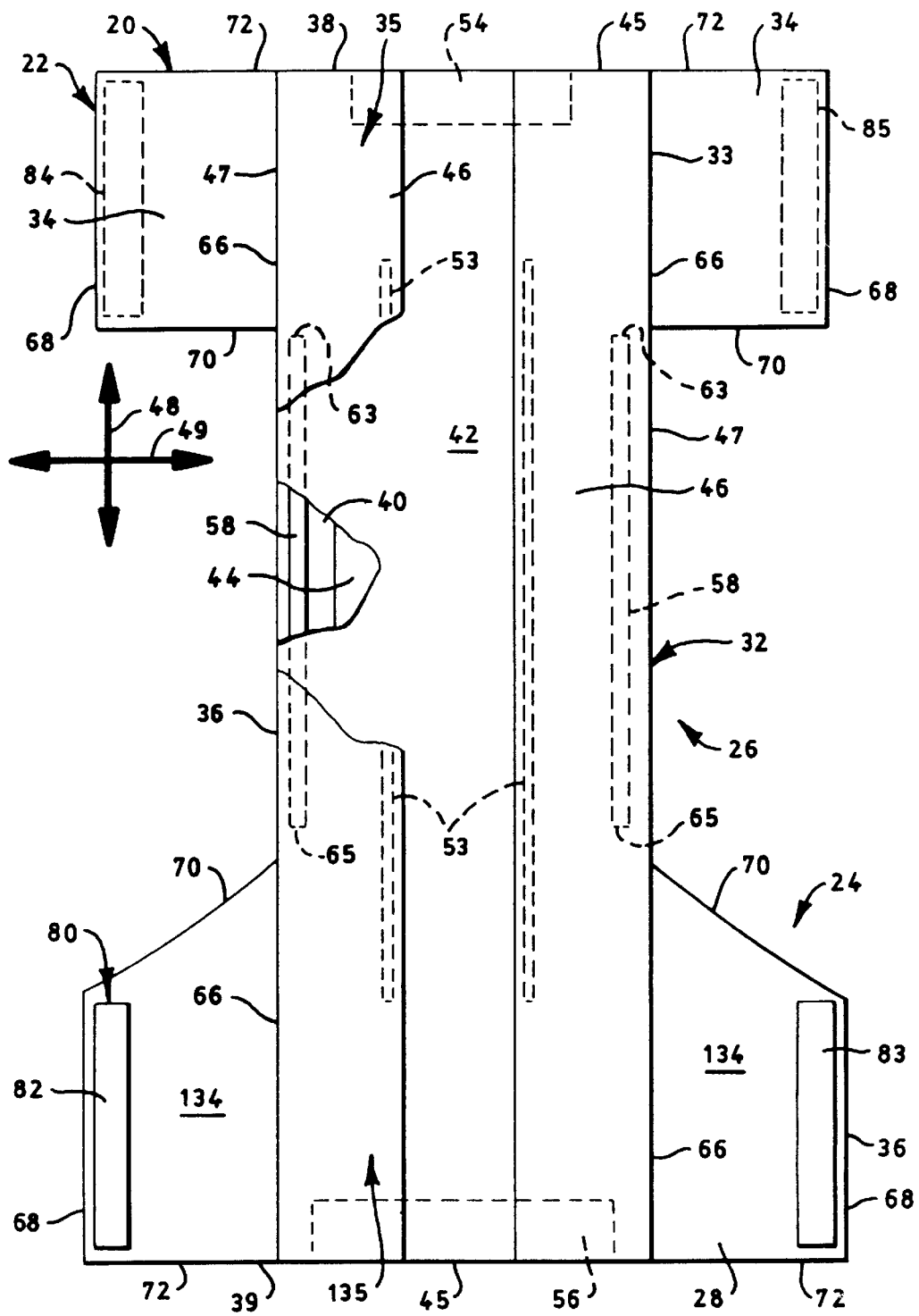
FIG. 6 illustrates a plan view similar to FIG. 5, but showing the surface of the training pant that faces the wearer when the training pant is worn, and with portions cut away to show the underlying features.

The illustrated absorbent chassis 32 comprises a composite structure 33 which can be rectangular or any other desired shape, a pair of transversely opposed front side panels 34, and a pair of transversely opposed back side panels 134. The composite structure 33 and side panels 34 and 134 may comprise two or more separate elements, as shown in FIG. 4, or be integrally formed. Integrally formed side panels and composite structure would comprise at least some common materials, such as the bodyside liner, flap composite, outer cover, other materials and/or combinations thereof, and could define a one-piece elastic, stretchable, or nonstretchable pant. The illustrated composite structure 33 comprises an outer cover 40, a bodyside liner 42 (FIGS. 4 and 6) which is connected to the outer cover in a superposed relation, an absorbent assembly 44 (FIG. 6) which is located between the outer cover and the bodyside liner, and a pair of containment flaps 46 (FIG. 6). The illustrated composite structure 33 has opposite linear end edges 45 that form portions of the front and back waist edges 38 and 39, and opposite linear side edges 47 that form portions of the side edges 36 of the absorbent chassis 32 (FIGS. 5 and 6). For reference, arrows 48 and 49 depicting the orientation of the longitudinal axis and the transverse axis, respectively, of the training pant 20 are illustrated in FIGS. 5 and 6.

With the training pant 20 in the fastened position as partially illustrated in FIG. 4, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent chassis 32 includes the transversely opposed front side panels 34 and a front center panel 35 (FIGS. 5 and 6) positioned between and interconnecting the side panels. The back waist region 24 of the absorbent chassis 32 includes the transversely opposed back side panels 134 and a back center panel 135 (FIGS. 5 and 6) positioned between and interconnecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 6) can be operatively joined with each containment flap 46 in any suitable manner as is well known in the art. The elasticized containment flaps 46 define an unattached edge which assumes an upright configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably although not necessarily includes a front waist elastic member 54, a rear waist elastic member 56, and leg elastic members 58, as are known to those skilled in the art (FIG. 6). The waist elastic members 54 and 56 can be operatively joined to the outer cover 40 and/or bodyside liner 42 along the opposite waist edges 38 and 39, and can extend over part or all of the waist edges. The leg elastic members 58 can be operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del. U.S.A.

The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Huntsman Packaging of Newport News, Va. U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 4 and 5, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60.

In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference. The primary pictorial image 61 is desirably positioned in the front waist region 22 along the longitudinal center line of the training pant 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pant can comprise elastomeric or nonelastomeric materials.

The absorbent assembly 44 (FIG. 6) is positioned between the outer cover 40 and the bodyside liner 42, which components can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 which can be rectangular or any other desired shape comprises a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 44 in an amount of from 0 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded along attachment lines 66 to the composite structure 33 of the absorbent chassis 32 in the respective front and back waist regions 22 and 24. More particularly, as shown best in FIGS. 5 and 6, the front side panels 34 can be permanently bonded to and extend transversely beyond the linear side edges 47 of the composite structure 33 in the front waist region 22, and the back side panels 134 can be permanently bonded to and extend transversely beyond the linear side edges of the composite structure in the back waist region 24. The side panels 34 and 134 may be attached using attachment means known to those skilled in the art such as adhesive, thermal or ultrasonic bonding. Alternatively, the side panels 34 and 134 can be formed as an integral portion of a component of the composite structure 33. For example, the side panels can comprise a generally wider portion of the outer cover, the bodyside liner, and/or another component of the absorbent chassis. The front and back side panels 34 and 134 can be permanently bonded together or be releasably attached to one another as illustrated by the fastening system 80.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the illustrated back side panels 134 have a continually decreasing length dimension moving from the attachment line 66 to the distal edge 68, as is best shown in FIGS. 5 and 6.

Each of the side panels 34 and 134 can include one or more individual, distinct pieces of material. In particular embodiments, for example, each side panel 34 and 134 can include first and second side panel portions that are joined at a seam, or can include a single piece of material which is folded over upon itself (not shown).

The side panels 34 and 134 desirably although not necessarily comprise an elastic material capable of stretching in a direction generally parallel to the transverse axis 49 of the training pant 20. Suitable elastic materials, as well as one process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The illustrated training pant 20 includes a fastening system 80 for refastenably securing the training pant about the waist of the wearer. The illustrated fastening system 80 includes first fastening components 82 and 83 that are adapted to refastenably connect to mating second fastening components 84 and 85. In one embodiment, one surface of each of the first fastening components 82 and 83 comprises a plurality of engaging elements that project from that surface. The engaging elements of the first fastening components 82 and 83 are adapted to repeatedly engage and disengage engaging elements of the second fastening components 84 and 85.

In one particular embodiment, the first fastening components 82 and 83 each comprise hook type fasteners and the second fastening components 84 and 85 each comprise complementary loop type fasteners. In another particular embodiment, the first fastening components 82 and 83 each comprise loop type fasteners and the second fastening components 84 and 85 each comprise complementary hook type fasteners. Alternatively, the fastening components can comprise interlocking similar surface fasteners; adhesive or cohesive fastening elements such as an adhesive fastener and an adhesive-receptive landing zone or material; or the like. Although the illustrated embodiments show the back waist region 24 overlapping the front waist region 22, which is convenient, the training pant 20 can also be configured so that the front waist region overlaps the back waist region.

Loop type fasteners typically comprise a fabric or material having a base or backing structure and a plurality of loop members extending upwardly from at least one surface of the backing structure. The loop material can be formed of any suitable material, such as acrylic, nylon, polypropylene or polyester, and can be formed by methods such as warp knitting, stitch bonding or needle punching. Loop type materials can also comprise any fibrous structure capable of entangling or catching hook type materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in U.S. Pat. No. 5,858,515 issued Jan. 12, 1999 to Stokes et al.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82–85 are available from commercial vendors such as Velcro Industries B.V., Amsterdam, Netherlands or affiliates thereof, and are identified as Velcro HTH-829 with a unidirectional hook pattern and having a thickness of about 0.9 millimeters (35 mils) and HTH-851 with a unidirectional hook pattern and having a thickness of about 0.5 millimeters (20 mils); and Minnesota Mining & Manufacturing Co., St. Paul, Minn. U.S.A., including specific materials identified as CS-600.

With particular reference to FIG. 6, the first fastening components 82 and 83 are desirably although not necessarily disposed on the inner surface 28 of the training pant 20 in the back waist region 24. The first fastening components 82 and 83 are desirably positioned along the distal edges 68 of the back side panels 134, and abutting or adjacent to the waist end edge 72. In certain embodiments, for example, the first fastening components 82 and 83 are located within about 2 centimeters, and more particularly within about 1 centimeter, of the distal edges 68, the waist end edges 72, and the leg end edges 70.

With particular reference to FIG. 5, the second fastening components 84 and 85 are desirably although not necessarily disposed on the outer surface 30 of the training pant 20 in the front waist region 22. The second fastening components 84 and 85 are sized to receive the first fastening components 82 and 83 and can be positioned along the distal edges 68 of the front side panels 34, and abutting or adjacent to the waist end edge 72. In certain embodiments, for example, the second fastening components 84 and 85 are located within about 2 centimeters, and more particularly within about 1 centimeter, of the distal edges 68, the waist end edges 72, and the leg end edges 70. Where the first fastening components 82 and 83 comprise loop type fasteners disposed on the inner surface 28 and the second fastening components 84 and 85 comprise hook type fasteners disposed on the outer surface 30, the first fastening components can be sized larger than the second fastening components to ensure coverage of the rigid, outwardly-directed hooks.

The fastening components 82–85 can be adhered to the side panels 34 and 134 by any means known to those skilled in the art such as adhesive bonds, ultrasonic bonds or thermal bonds. The fastening components can comprise separate fastening elements or can comprise distinct regions of an integral material. For example, the training pant 20 can include an integral second fastening material disposed in the front waist region 22 for refastenably connecting to the first fastening components 82 and 83 at two or more different regions, which define the second fastening components 84 and 85 (FIG. 3). In a particular embodiment, the fastening components can comprise integral portions of the waist regions. For instance, one of the elastomeric front or back side panels can function as second fastening components in that they can comprise a material that is releasably engagable with fastening components disposed in the opposite waist region.

The fastening components are desirably rectangular, although they may alternatively be square, round, oval, curved or otherwise non-rectangularly shaped. In particular embodiments, each of the fastening components 82–85 defines a length dimension aligned generally parallel with the longitudinal axis 48 of the training pant 20 and a width dimension aligned generally parallel with the transverse axis 49 of the training pant. For a child of about 9 to about 15 kilograms (20–30 pounds), for example, the length dimension of the fastening components is desirably from about 5 to about 13 centimeters, such as about 10 centimeters, and the width dimension is desirably from about 0.5 to about 3 centimeters, such as about 1 centimeter. With particular embodiments, the fastening components can have a length-to-width ratio of about 2 or greater, such as about 2 to about 25, and particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

When the fastening components 82–85 are releasably engaged, the side edges 36 of the absorbent chassis 32 in the crotch region 26 define the leg openings 52, and the waist edges 38 and 39 of the absorbent chassis, including the waist end edges 72 of the side panels, define the waist opening 50. For improved formation of the leg openings 52, it is desirable in some embodiments for the front side panels 34 to be longitudinally spaced from the back side panels 134 (see FIGS. 5 and 6). For example, the front side panels 34 can be longitudinally spaced from the back side panels 134 by a distance equal to about 20 percent or greater, particularly from about 20 to about 60 percent, and more particularly from about 35 to about 50 percent, of the overall length dimension of the absorbent article.

When connected, the fastening components 82–85 form refastenable seams 88 (FIG. 4) that desirably although not necessarily extend substantially the entire distance between the waist opening 50 and the leg openings 52. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82–85 can be formed to cover about 80 to 100 percent, and more particularly about 90 to about 98 percent, of the distance between the waist end edge 70 and the leg end edge 72 of the side panels 34 and 134. In other embodiments, the fastening components can comprise a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

For the refastenable seams 88 to be located at the sides of the wearer, it is particularly desirable for the transverse distance between the first fastening components 82 and 83 to be substantially equal to the transverse distance between the second fastening components 84 and 85. The transverse distance between a set of fasteners is measured parallel to the transverse axis 49 between the longitudinal center lines of the fasteners.

An exemplary embodiment of an assembly section 100 for making a continuous stream of partially assembled, discrete garments 102 is illustrated in FIG. 1. The specific equipment and processes used in the assembly section 100 can vary greatly depending on the specific type of garment being manufactured. The particular process and apparatus described in relation to FIG. 1 is specifically adapted to manufacture training pants 20 of the type illustrated in FIG. 4.

The various components of the training pant can be connected together by any means known to those skilled in the art such as, for example, adhesive, thermal and/or ultrasonic bonds. Desirably, most of the components are connected using ultrasonic bonding for improved manufacturing efficiency and reduced raw material costs. Certain garment manufacturing equipment which is readily known and understood in the art, including frames and mounting structures, ultrasonic and adhesive bonding devices, transport conveyors, transfer rolls, guide rolls, tension rolls, and the like, have not been shown in FIGS. 1 and 2. Suitable absorbent supply mechanisms, web unwinds, conveyor systems, registration systems, drives systems, control systems and the like, for use with the present process are disclosed in U.S. Pat. No. 5,766,389 issued Jun. 16, 1998 to Brandon et al., which is incorporated herein by reference. Also, the outer cover graphics 61 are not shown in FIGS. 1, 2 and 7.

A continuous supply of material 104 used to form the bodyside liner 42 is provided from a supply source 106. The supply source 106 can comprise for example any standard unwind mechanism, which generally includes a pair of spindles, a festoon assembly, and a dancer roll for providing bodyside liner material 104 at a desired speed and tension.

Various components can be disposed on and/or bonded to the bodyside liner material 104 as the material travels in a machine direction identified by arrow 108. In particular, a surge layer can be provided at an application station 110 and disposed on and/or bonded to the bodyside liner material 104. The surge layer can comprise either a continuous web or discrete sheets. Additionally, a containment flap module 112 can be provided downstream of the supply source 106 for attaching pre-assembled containment flaps to the bodyside liner material 104. As various components are added in the assembly section 100, a continuously moving product assemblage 113 is formed. The product assemblage 113 will be cut downstream to form the partially assembled, discrete training pants 102.

A plurality of absorbent assemblies 114 can be provided from a suitable supply source 115. The supply source 115 can be any conventional mechanism for supplying the absorbent assemblies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent assemblies 114 can be disposed intermittently on the continuously moving bodyside liner material 104, one for each training pant. The position of the absorbent assemblies 114 can be registered with the position of the surge material, if employed. The absorbent assemblies 114 can be bonded to one or more other components using adhesives or other suitable means. Alternatively, composite absorbent materials can be fed into the converting process from rolls or compressed packages, such as festooned bales.

Continuous webs of material 116 used to form the side panels 34 and 134 can be provided from suitable supply sources 117. The supply sources 117 can comprise one or more standard unwind mechanisms. The side panel material 116 can be cut into individual strips 118 and positioned partially on the bodyside liner material 104 using an applicator device 120. In the cross machine direction, the individual strips 118 desirably extend laterally outward from the bodyside liner material 104 (see FIGS. 1 and 7) and overlap the bodyside liner material by an amount such as about 2 or more centimeters to permit bonding of the strips to the bodyside liner and/or the containment flap material. In the machine direction 108, the position of the strips 118 can be registered relative to the absorbent assemblies 114 so that the product assemblage 113 can be cut between the absorbent assemblies with each strip 118 of side panel material 116 forming both a front side panel 34 and a back side panel 134 of consecutive garments 102.

One suitable applicator device 120 is disclosed in U.S. Pat. No. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly 122 and a rotatable transfer roll 124. The cutting assembly 122 employs a rotatable knife roll 126 and a rotatable vacuum anvil roll 128 to cut individual strips 118 from the continuous side panel material 116. The strips 118 cut by a blade on the knife roll 126 can be maintained on the anvil roll 128 by vacuum and transferred to the transfer roll 124.

The rotatable transfer roll 124 can comprise a plurality of rotatable vacuum pucks 130. The vacuum pucks 130 receive the strips 118 of material 116 from the cuffing assembly 122 and rotate and transfer the strips to the continuously moving bodyside liner material 104. When the strips 118 are positioned as desired relative to the bodyside liner material 104, the strips are released from the pucks 130 by extinguishing the vacuum in the pucks. The pucks 130 can continue to rotate toward the cutting assembly 122 to receive other strips.

As disclosed by Van Gompel et al., the material 116 used to form the side panels can alternatively be provided in continuous form and pressurized fluid-jets or a rotary die cutter can be employed to cut the material to form leg openings 52. Still alternatively, the side panels 34 and 134 of the training pant 20 can be provided by portions of the bodyside liner 42 and/or outer cover 40.

A continuous supply of material 140 used to form the outer cover 40 can be provided from a supply roll 142 or other suitable source. The outer cover material 140 can be transported over a laminator roll 144 and married with the bodyside liner material 104. The absorbent assemblies 114 are thereby sandwiched between the continuous materials 104 and 140. The inward portions of the strips 118 of side panel material 116 can also be disposed between the bodyside liner material 104 and the outer cover material 140. Alternative configurations for attaching the side panel material 116 are disclosed by Van Gompel et al. Various components such as leg elastics 58 or waist elastics 54 and 56 can be bonded to the outer cover material 140 at an application station 146 prior to uniting the bodyside liner and outer cover materials 104 and 140. Alternatively, leg elastics or waist elastics can be initially bonded to the bodyside liner material 104 or another material.

Bonding devices 148 such as ultrasonic bonders can be employed downstream of the laminator roll 144 to bond the bodyside liner material 104, side panel material 116 and outer cover material 140. For example, these materials can be transported between a rotary ultrasonic horn and an anvil roll. Suitable rotary ultrasonic horns are described in U.S. Pat. No. 5,110,403 to Ehlert, which is incorporated herein by reference. Such rotary ultrasonic horns generally have a diameter of from about 5 to about 20 centimeters and a width of from about 2 to about 15 centimeters. Alternatively, the ultrasonic horn may be a stationary ultrasonic horn as are also known to those skilled in the art. Other suitable ultrasonic horns and ultrasonic bonders are commercially available from Branson Sonic Power Company, Danbury, Conn. U.S.A. The bonding devices 148 could otherwise be a thermal or adhesive bonder as are well known.

The continuously moving product assemblage 113 next advances to a fastener application station 150 where fastening components 82–85 are bonded to the strips 118 of side panel material 116. The location of the fastening components on the composite is a function in part of the configuration of the assembly section 100. The illustrated assembly section 100 is configured so that the upwardly facing surface of the product assemblage 113 will become the outer surface 30 of the training pant 20 and the downwardly facing surface will become the inner surface 28. Moreover, the illustrated assembly section 100 is configured to produce partially assembled training pants 102 having the front waist region 22 of a leading garment connected to the back waist region 24 of a trailing garment. The process could alternatively employ any combination of different orientations. For example, the upwardly facing surface of the product assemblage could form the inner surface 28 of finished garments. Additionally or alternatively, the back waist region 24 of a leading garment can be connected to the front waist region 22 of the trailing garment, or the garments can be arranged in a front-to-front/back-to-back relationship. Still alternatively, the assembly section 100 could be constructed as a cross-machine direction process wherein the longitudinal axis 48 of each garment could be perpendicular to the machine direction 108 during part or all of the assembly process.

Figure 7:
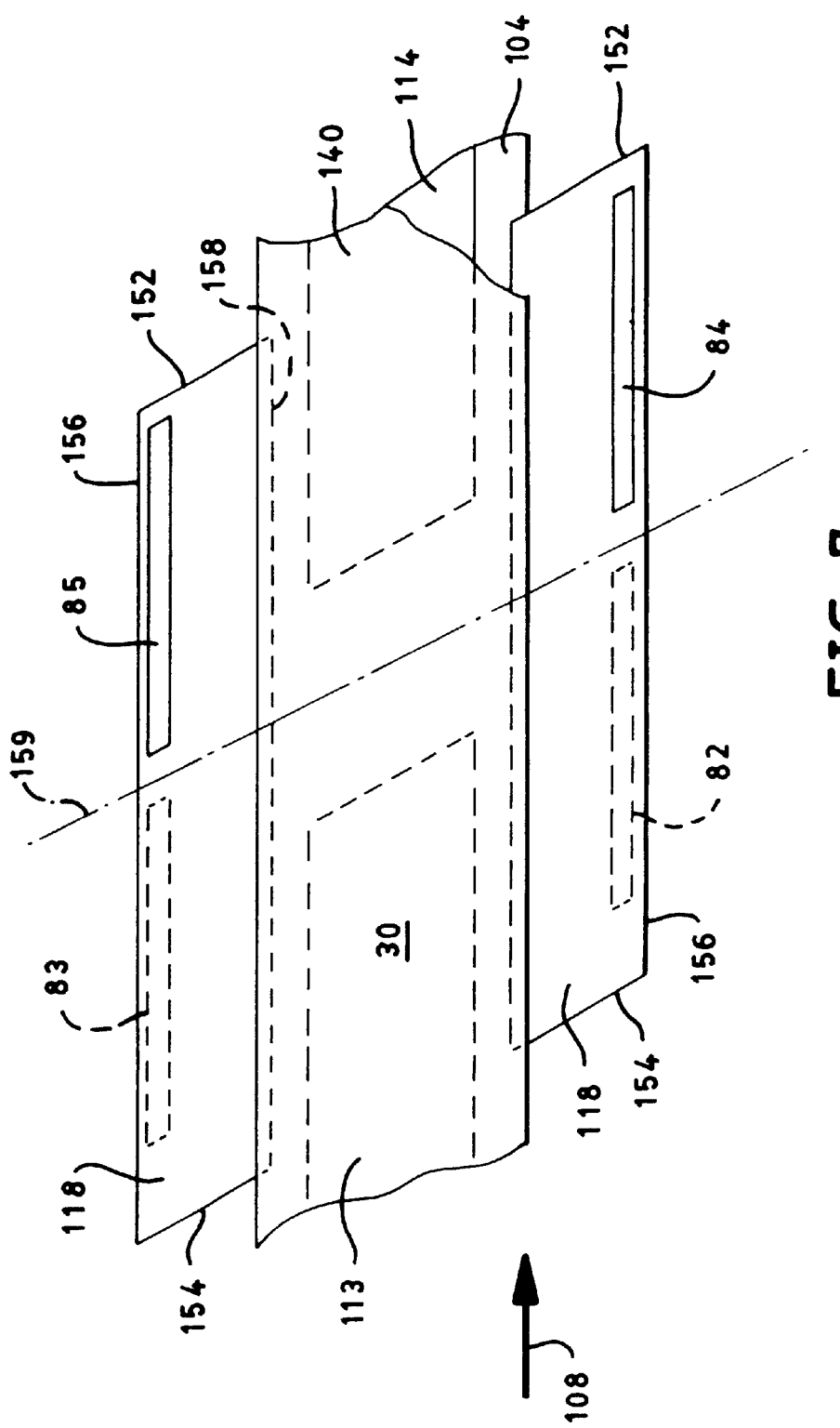
FIG. 7 illustrates a portion of a continuously moving assemblage at one point in the assembly section illustrated in FIG. 1.

The location of the fastening components 82–85 in this embodiment is best illustrated in FIG. 7, which shows a portion of the product assemblage 113 which is moving in the direction of arrow 108 immediately following the fastener application station 150. Each individual strip 118 of side panel material 116 defines a leading edge 152, a trailing edge 154, a distal edge 156 and an interior edge 158. A dashed line 159 illustrates the location at which the product assemblage 113 can subsequently be cut to provide the discrete training pants 102. Based on the illustrated orientation of the continuously moving product assemblage 113, the first fastening components 82 and 83 can be bonded to the underside of the strips 118 and the second fastening components 84 and 85 can be bonded to the top of the strips. Additionally, the first fastening components 82 and 83 can be disposed relatively closer to the trailing edge 154 and the second fastening components 84 and 85 can be disposed relatively closer to the leading edge 152. The first fastening components 82 and 83 can be spaced in the machine direction 108 from the second fastening components 84 and 85 so that the cut line 159 passes therebetween.

With reference again to FIG. 1, continuous webs of second fastener material 160 used to form the second fastening components 84 and 85 can be provided from supply rolls 162 or other suitable sources. The second fastener materials 160 can be cut into individual second fasteners 84 and 85 by cutting assemblies 164 or other suitable devices. The illustrated cutting assemblies 164 include rotatable knife rolls 166, rotatable vacuum anvil rolls 167, and rotatable backing rolls 168. The continuous second fastener materials 160 can be cut by blades on the knife rolls 166, maintained on the anvil rolls 167 by vacuum, and disposed on the top surfaces of the strips 118 of side panel material 116.

Similarly, continuous webs of first fastener material 170 used to form the first fastening components 82 and 83 can be provided from supply rolls 172 or other suitable sources. The first fastener materials 170 can be cut into individual first fasteners 82 and 83 by cutting assemblies 174 or other suitable devices. The illustrated cutting assemblies 174 include rotatable knife rolls 176, rotatable vacuum anvil rolls 177, and rotatable backing rolls 178. The continuous first fastener materials 170 can be cut by blades on the knife rolls 176, maintained on the anvil rolls 177 by vacuum, and disposed on the undersides of the strips 118 of side panel material 116.

Other arrangements can be used to attach the fastening components 82–85. For example, the fastening components can be applied to the side panel material 116 prior to uniting the side panel material with the bodyside liner material 104 and/or the outer cover material 140; the fastening components can be applied to the bodyside liner material 104 and/or outer cover material 140, whether separate side panels are used or not; portions of other components such as the bodyside liner and/or outer cover can form one or more of the fastening components; the separate side panels or integral side panels can themselves form one or more of the fastening components; the fastening components can be attached as pre-engaged composites 82, 84 and 83, 85; or the like.

After the fastening components are disposed on the strips 118 of side panel material 116, bonding devices 180 such as ultrasonic bonders can be employed to bond the fastening components to the strips. For example, the strips 118 can be transported between a rotary ultrasonic horn and an anvil roll, which devices are positioned on each side of the process at the cross machine direction location, that is the transverse location, of the fastening components 82, 84 and 83, 85. Particular ultrasonic bond patterns comprising individual, circular bonds which are compatible with mechanical fastening materials are disclosed in U.S. Pat. No. 5,660,666 issued Aug. 26, 1997 to Dilnik et al., which is incorporated herein by reference. Efficient arrangements for attaching the fastening components with nonadhesive bonding devices are further described in U.S. patent application Ser. No. 09/855,484, filed on May 15, 2001 by J. D. Coenen et al. and titled "Methods For Making Garments With Fastening Components," which is incorporated herein by reference. For secure attachment, it may be desirable to attach the fastening components with both adhesive and thermal bonds. Suitable attachment adhesives are available from commercial vendors such as Findley Adhesive, Inc., Wauwatosa, Wis. U.S.A.

In particular embodiments, the bonding devices 180 can provide timed, non-uniform bonding of the fastening components to the side panel material 116. The degree of bonding, such as the number of bonds per unit area or the bond strength per unit area, can be greater in certain target areas compared to non-target areas. Enhanced bonding in target areas can be beneficial particularly near the waist and leg openings 50 and 52 to reduce delamination of the fastening components from the side panel material 116. Thus, the bonding devices 180 can be adapted to create relatively more bonds or stronger bonds between the fastening components 82–85 and the side panel material 116 when the side panel material 116 reaches a particular machine direction 108 location. In one particular embodiment, the target areas correspond to portions of the fastening components 82–85 near the waist edges 38 and 39. The bonding devices 180 can be registered to provide a relatively higher degree of bonding which begins while disposed on one fastening component (such as 84 in FIG. 7), continues through the region where the product assemblage 113 will subsequently be cut (see cut line 159 in FIG. 7), and ends after being disposed on another fastening component (such as 82). Alternatively, the bonding devices 180 can destroy engaging elements of the fastening components 82–85 in the target areas, so that the fastening components will be less able to aggressively attach to one another in the target areas.

The strips 118 of side panel material 116 can be trimmed if desired, for example to provide angled and/or curved leg end edges 70 in the back waist region 24 (FIGS. 5 and 6). To this end, the assembly section 100 can include a die cutting roll 182 and a backing roll 184. In the illustrated embodiment, a portion of each strip 118 is trimmed from the trailing edge 154 (FIG. 7) in order to form the angled and/or curved leg end edges 70 in the back waist region 24.

The method and apparatus to this point provides a continuous web of interconnected and partially assembled training pants moving in the direction indicated by arrow 108. This continuously moving product assemblage 113 is passed through a cutter 186 which selectively cuts the web into discrete, partially assembled training pants 102. Such cutters 186 are generally known to those skilled in the art and can include, for example, the combination of a cutting roll 187 and an anvil roll 188 through which the web travels (FIG. 2). The anvil roll 188 can include a hardened steel rotating roll while the cutting roll 187 can include one or more flexible hardened steel blades clamped onto another rotating roll. The pinching force between the blade on the cutting roll 187 and the anvil roll 188 creates the cut. The cutting roll 187 can have one or more blades depending upon the desired distance between the cuts. The cutter 186 can further be configured to provide a spacing between the individual cut pieces after they are cut. Such a spacing can be provided by transferring the cut pieces away from the cutter at a higher speed than the speed at which the web is provided to the cutter.

The discrete training pants 102 can then be folded at a folding station 200 using any suitable folding mechanism 202 (FIG. 2). The training pants 102 can be folded about a fold line generally bisecting the training pants. As such, the waist regions 22 and 24 of each training pant 102 are positioned in facing relationship with the side panels 34 and 134 extending laterally outward relative to the longitudinal axis 48 of the training pant. The fold line can extend in a lateral direction through the crotch region 26 of the training pant. Desirably, each discrete training pant 102 is consistently folded about the fold line such that the front and back waist edges 38 and 39 of the training pant align with each other.

Figure 8:
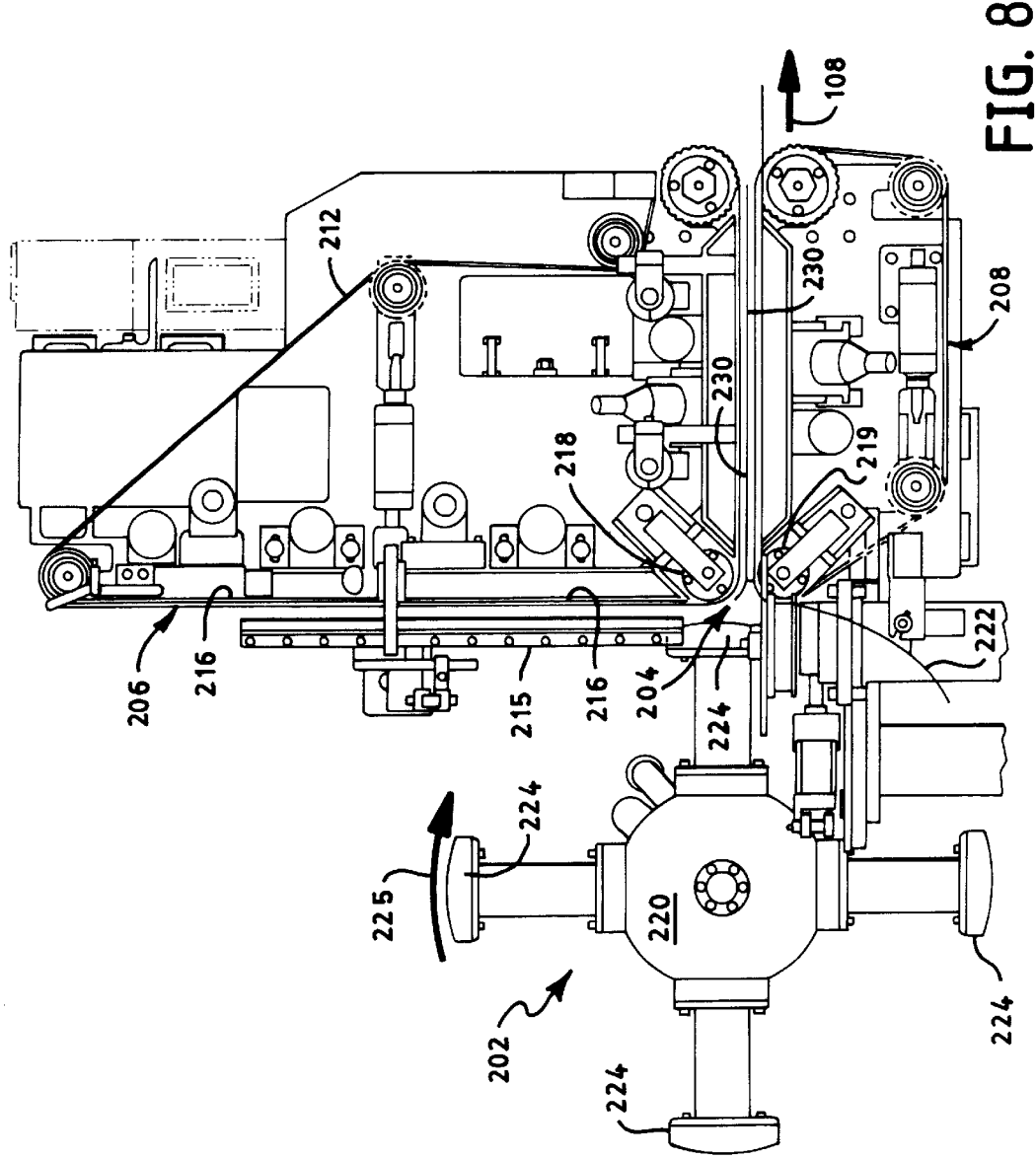
FIG. 8 illustrates an enlarged side view of the folding section shown in FIG. 2.
Figure 9:
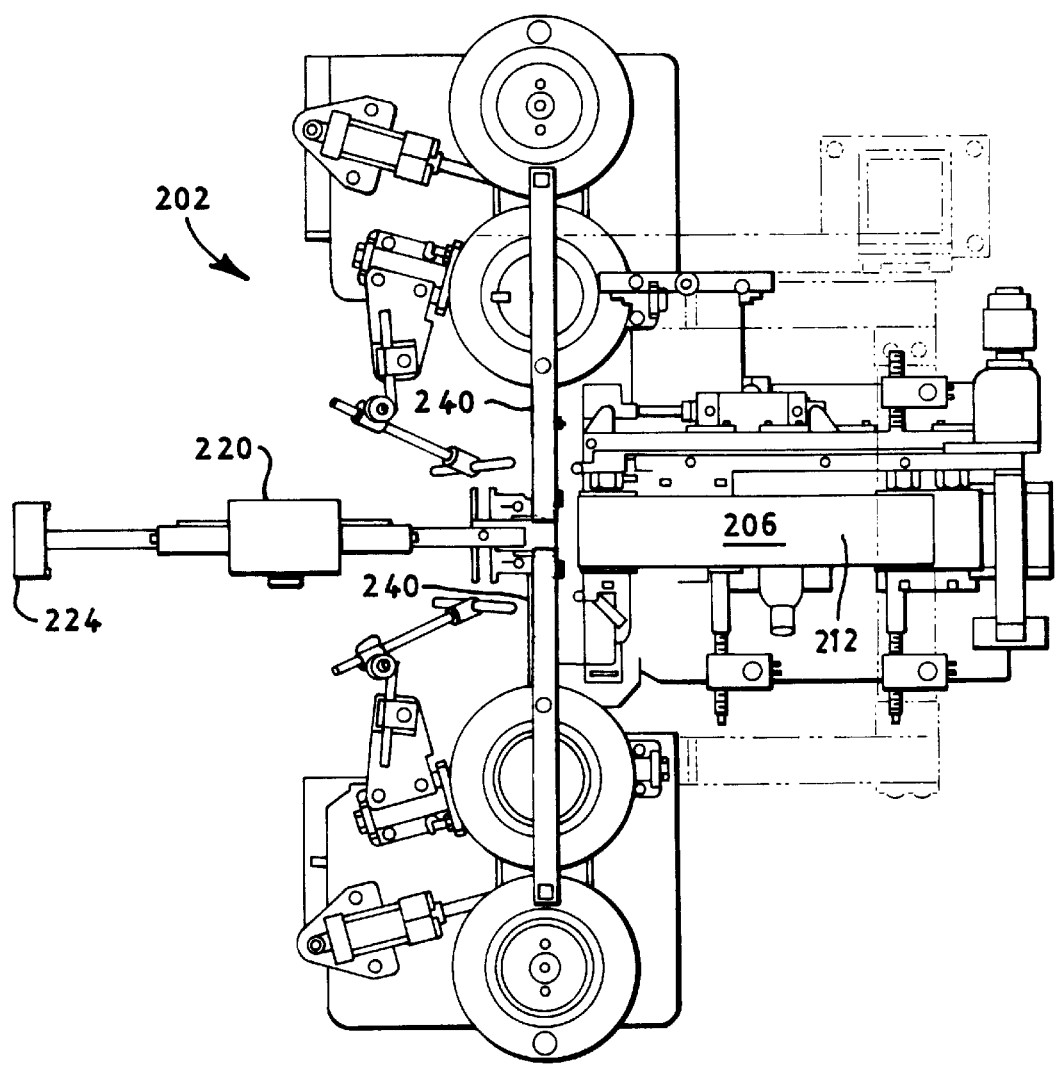
FIG. 9 illustrates a top view of a portion of the folding section shown in FIG. 2.

A variety of folding mechanisms 202 can be used, such as blade folders, linear folders, book folders, tucker blades or the like. The specific type selected for a given application may depend upon the type of garment being manufactured and the type of fastening mechanism used to secure the garment in a pant configuration. An embodiment of a blade folding mechanism 202 adapted for use with garments incorporating refastenable fastening components 82–85 is illustrated in FIGS. 2, 8 and 9. The illustrated folding mechanism 202 controls the side panels 34 and 134 during folding so that the refastenable fastening components 82–85 are unlikely to engage one another or engage another material during the folding operation. Other arrangements for maintaining separation of the side panels and fastening components during folding are disclosed in U.S. patent application Ser. No. 09/855,981, filed on May 15, 2001 by J. D. Coenen et al. and titled "Folding And Manufacture Of Pants," which is incorporated herein by reference.

The illustrated blade folding mechanism 202 comprises a plurality of rotating folding or tucker blades which are configured to contact the training pant 102 along the fold line. Rotation of the folding blades can force the training pant 102 into a nip 204 between two rotating folding conveyors 206 and 208 causing the training pants to fold about the fold line. The folding conveyors 206 and 208 can form part of a transport system for moving the folded training pants 102 in the machine direction 108. The folded training pants 102 are illustrated as being transported in the machine direction 108 with the crotch region 26 leading the waist regions 22 and 24. Alternatively, the process and apparatus could be modified so that the waist regions lead the crotch region (not shown).

With reference to FIGS. 2, 8 and 9, the series of unfolded, discrete training pants 102 can be transferred from the vacuum anvil roll 188 of the cutter 186 to the upper folding conveyor 206. The training pants 102 can be held by vacuum on the upper folding conveyor 206 and transported toward the nip 204 formed between the folding conveyors 206 and 208. While being transported toward the nip 204, the side panels 34 and 134 can be smoothed out or straightened if desired by various means including fluid stabilizing devices. For example, air knives 215 (FIG. 8), air bars, air nozzles or the like can be mounted in proximity to the upper folding conveyor to provide a stream of fluid directed toward the side panels to stabilize and/or straighten the side panels. The air knives 215 can blow the side panels 34 and 134 against skid plates 216 positioned transversely outward from the upper folding conveyor belt 212. Alternatively, or in addition thereto, the upper folding conveyor 206 can incorporate fluid stabilizing devices consisting of fluid manifolds operatively connected to a high pressure fluid source to fluidly shake the side panels. The fluid stabilizing devices desirably prevent folding of the side panels 34 and 134 as the training pant 102 moves along the upper folding conveyor 206. Sensing devices can also be employed at this point to detect products that have folded side panels or that are misaligned relative to the machine center line.

The product folding nip 204 can be formed between a timed vacuum nose roll 218 of the upper folding conveyor 206 and a timed vacuum nose roll 219 of the lower folding conveyor 208 (FIGS. 2 and 8). As the leading edge of a pant 102 is introduced onto the upper nose roll 218, compressed air can be introduced inside the nose roll to negate vacuum draw of the nose roll. This allows the leading edge of the pant to pass by the nose roll 218 without getting sucked into the nip 204. Alternatively of course, the vacuum source can be temporarily disconnected from the nose roll 218. Any suitable control system can be used to repeatedly activate and deactivate vacuum operation of the nose rolls 218 and 219. In particular embodiments, rotary valves can be employed to cycle vacuum to the nose rolls 218 and 219.

A product control drum 220 can guide the leading half of the training pant 102 onto a curved transfer plate 222 (FIGS. 2 and 8). The product control drum 220 can comprise a plurality of vacuum pucks 224 which rotate in the direction of arrow 225. The illustrated product control drum 220 includes four vacuum pucks 224 to guide four training pants 102 per revolution. Rotation of the product control drum 220 can be timed so that a vacuum puck 224 grabs the leading half of a training pant 102 and transfers the leading edge onto the curved transfer plate 222. The absorbent chassis 32 and/or side panels 134 of the leading half can be carried on a vacuum puck 224 past the nose roll 219 of the lower folding conveyor 208. Compressed air can be introduced inside this lower nose roll 219 at this point to negate vacuum draw and permit the entire leading edge and side panels 134 to transfer onto the curved transfer plate 222. Alternatively of course, the vacuum source can be temporarily disconnected from the nose roll 219.

With reference to FIG. 9, the folding mechanism 202 can comprise a pair of opposed tucker blades 240 that move in an orbital manner to pass through the vertical path of the training pant 102. The tucker blades 240 can contact the crotch region 26 of the pant 102 and insert the crotch region into the folding nip 204. As this happens, the leading half of the pant 102 reverses direction over the curved transfer plate 222 and is pulled into the nip 204. The vacuum puck 224 can cease drawing vacuum at this point to release the leading half. Correspondingly, the trailing half of the pant 102 is pulled around the upper nose roll 218. Thus, both halves of the training pant 102 can change from motion in a generally vertical plane to motion between the folding conveyors 206 and 208 in a generally horizontal plane.

Figure 10:
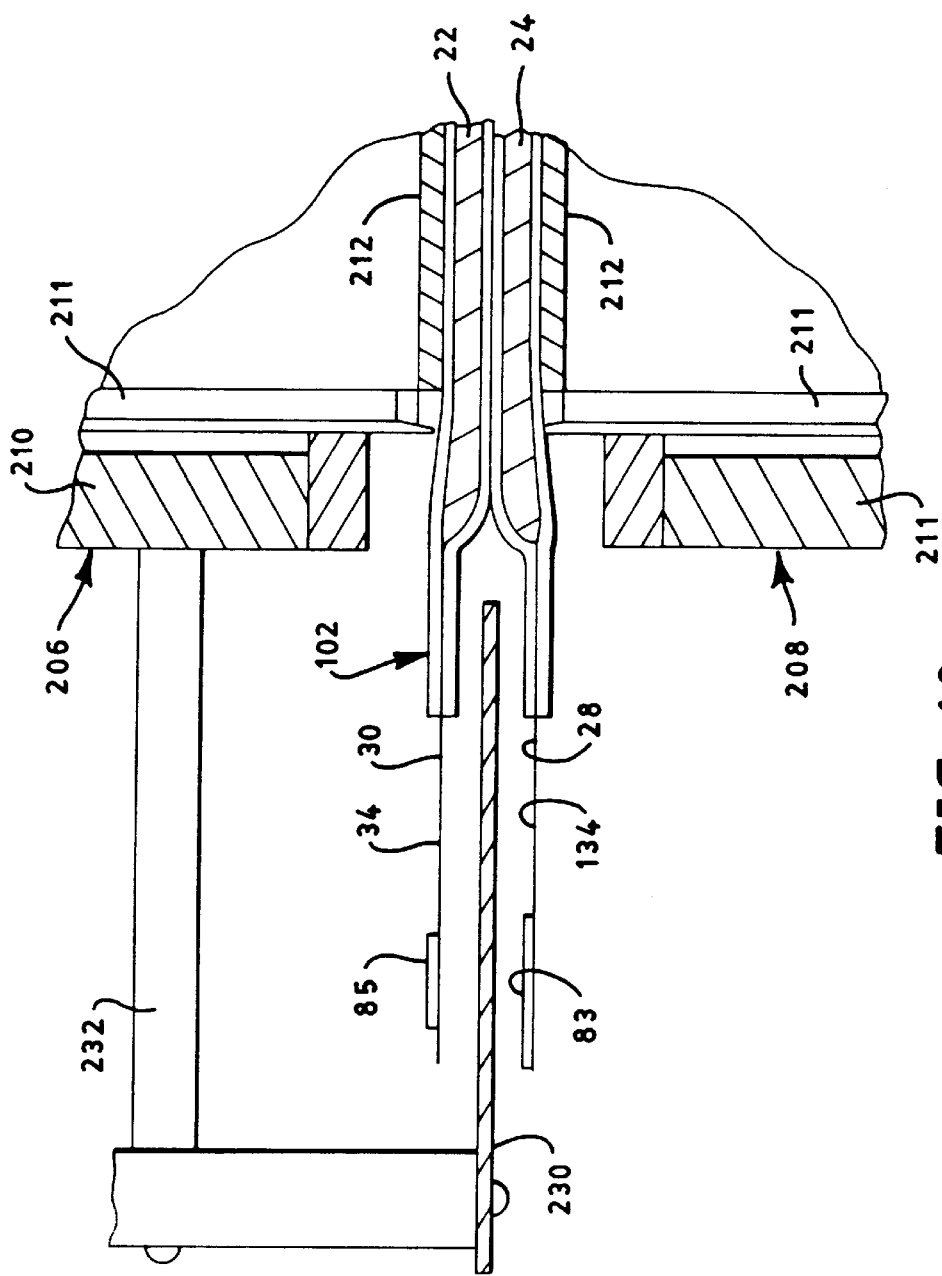
FIG. 10 illustrates an enlarged section view of a portion of a training pant at a position within the folding section shown in FIGS. 2, 8 and 9.

The illustrated folding mechanism 202 can maintain separation between the front and back side panels 34 and 134. As the pant 102 enters the folding nip 204, compressed air can be shut off to the upper nose roll 218 so that the side panels 34 of the trailing half are drawn by vacuum to the upper nose roll. The trailing side panels 34 are thus drawn to the upper nose roll 218 and follow its rotation around the roll and over side panel separation plates 230 (FIGS. 8 and 10). Similarly, as the leading half of the pant 102 is pulled into the folding nip 204, compressed air can be shut off to the lower nose roll 219 so that the side panels 134 of the leading half are drawn by vacuum to the lower nose roll. The leading side panels 134 are thus drawn to the lower nose roll 219 and follow its rotation around the roll and beneath the side panel separation plates 230.

FIG. 10 illustrates a portion of a partially assembled training pant 102 positioned between the upper and lower folding conveyors 206 and 208 at a location downstream of the nose rolls 218 and 219. At this point, the training pant 102 has been folded in half and is being transported in the machine direction 108 by the conveyors 206 and 208. The illustrated folding mechanism 202 can thus maintain the front side panels 34 separated from the back side panels 134 during folding.

Each folding conveyor 206 and 208 as illustrated in greater detail in FIG. 10 can comprise a frame structure 210, a plurality of rotatable pulleys 211 associated with the frame structure, and a continuous belt 212 carried on the pulleys. A drive system and conveyor shaft (not shown) can be used to rotatively drive one or more of the pulleys. The folding conveyors 206 and 208 can comprise vacuum conveyors as are well known in the art, in which case the continuous belt can be formed of a fluid permeable material. The folding conveyors desirably transport the training pants 102 with the longitudinal center line of the training pants traveling on the longitudinal center line of the conveyors. As depicted, the front and back side panels 34 and 134 can project laterally outward from the frame structure 210, outstretched in the cross-machine direction.

While traveling on the folding conveyors 206 and 208, the side panels 34 and 134 can be smoothed out or straightened if desired by various means including fluid stabilizing devices (not shown in FIG. 10). Suitable fluid stabilizing devices can comprise air knives, air bars, air nozzles, vacuum devices or the like to provide a stream of fluid directed toward the side panels. The fluid stabilizing devices can be incorporated within either or both of the folding conveyors 206 and 208 or can comprise separate devices positioned in proximity to the conveyors.

As a result of the illustrated folding mechanism 202, the front waist region 22 and front side panels 34 of the partially assembled training pant 102 are disposed above the back waist region 24 and back side panels 134. The first fastening components 82 and 83 are disposed on the inner surface 28 of the back side panels 134 and the second fastening components 84 and 85 are disposed on the outer surface 30 of the front side panels 34. In the illustrated embodiment, the transverse linear distance between the first fastening components 82 and 83 is the same as the transverse linear distance between the second fastening components 84 and 85.

The separation plates 230 can extend in the machine direction 108 to maintain separation between the front and back side panels 34 and 134. The separation plates 230 can comprise a low friction material or coating, such as: stainless steel; teflon; aluminum; ultra-high molecular weight polyethylene (UHMW-PE); polyoxymethylene (acetals), for instance a homopolymer available from E. I. Du Pont de Nemours and Company, Wilmington, Del. USA under the tradename DELRIN; or the like. In particular embodiments, the separation plates 230 can comprise a thin layer of teflon, UHMW-PE, DELRIN or the like glued to a plate formed of steel, aluminum or the like. The separation plates can be mounted using suitable support members 232 (FIG. 10) to either the folding conveyors 206 or 208 or other suitable frame structures (not shown).

From the folding station 200, the continuous stream of discrete, partially assembled and folded training pants 102 enters a seaming section 250, an embodiment of which is shown in FIG. 3. The seaming section 250 can encompass processes and apparatus for controlling the unattached side panels 34 and 134, modifying at least one waist region 22 or 24 to change the transverse distance between the fastening components on that waist region, guiding the waist regions into an overlapping orientation to form a lap seam, and bonding the waist regions together.

In the embodiment shown in FIG. 4, the side panels are refastenably bonded together using mating mechanical fastening components 82–85, although other refastenable bonding arrangements can also be used. The seaming section 250 can thus convert the partially assembled and folded training pants 102 into prefastened training pants 20 each having a waist opening 50 and a pair of leg openings 52 (FIG. 4). The illustrated seaming section 250 could of course be inverted so that the lower side panel forms the inner side panel of the lap seam (not shown). From the seaming section 250, the training pants 20 can be processed through various finishing stations 254, for operations such as side panel tucking, packaging, or the like.

The terms "upper" and "lower" are provided for ease of understanding, and it should be recognized that the spatial arrangement of the elements being described could be inverted or arranged in another manner. Use of the terms "vertical" and "horizontal" and variations thereof have their usual meaning, however, the present invention contemplates that vertical surfaces can be "generally vertically" disposed if desired and would thus be oriented between the true vertical position and about a 45 degree position relative to the true vertical position. The same interpretation for "generally horizontally" disposed means an orientation between the true horizontal and about a 45 degree position relative thereto.

The partially assembled training pants 102 can be transported in the machine direction 108 through the seaming section 250 by a transport system, such as conveyors or other suitable means. In the illustrated embodiment, the training pants 102 are transferred from the upper and lower folding conveyors 206 and 208 (FIGS. 2 and 8–10) to upper and lower alignment conveyors 256 and 258 (FIGS. 3 and 11–14). The alignment conveyors 256 and 258 can transport the training pants 102 through upper and lower side panel positioning devices 260 and 262 (FIGS. 3 and 11–13). Suitable conveyor mechanisms such as vacuum conveyors or non-vacuum conveyors are available from various commercial vendors. Alternatively, the transport system can comprise any means to transport the folded products.

Formation of the side panel lap seam will be described in greater detail with reference to FIGS. 11–13, which illustrate section views of a training pant 102 at a series of continually advancing positions within the seaming section 250. The illustrated upper side panel positioning device 260 is adapted to invert the second fastening components 84 and 85 in preparation for the front side panels 34 forming the interior side panels of the lap seam. The illustrated lower side panel positioning device 262 is adapted to modify the back waist region 24 to transversely displace the first fastening components 82 and 83 inward toward one another. The back side panels 134 will form the exterior side panels of the lap seam in this embodiment. The description will focus on the formation of a lap seam and bonding the side panels 34 and 134 together on one side of the training pant 102, although it should be recognized that a lap seam can be formed on the other side of the training pant in a similar manner. The refastenable seams 88 can be formed simultaneously or sequentially on the right and left sides of the pant 102.

Figure 11:
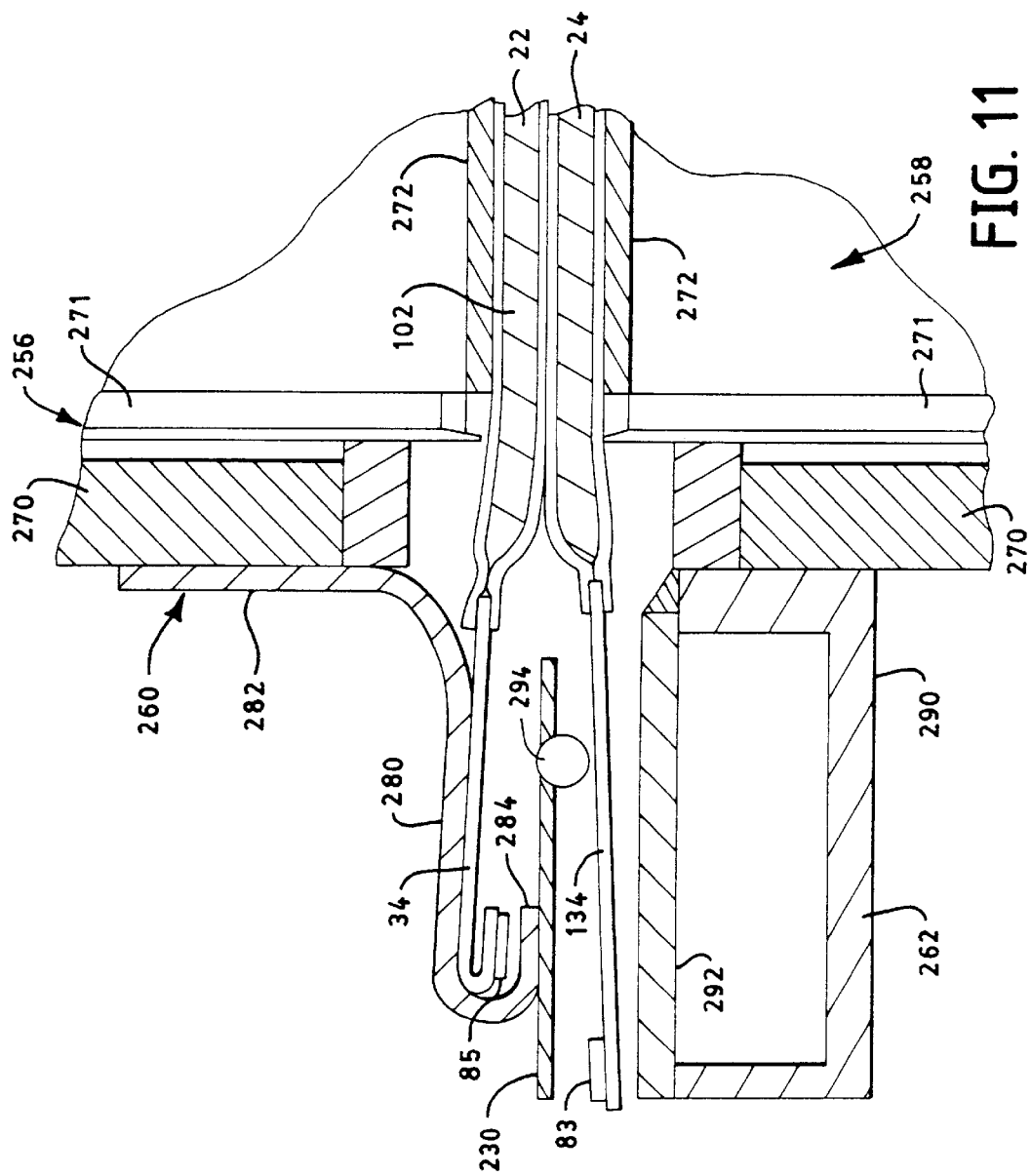
FIGS. 11–13 illustrate enlarged section views of a portion of a training pant at a series of positions within the seaming section shown in FIG. 3.

FIG. 11 illustrates the training pant 102 positioned between the upper and lower alignment conveyors 256 and 258 at a location downstream of the location illustrated in FIG. 10. Each alignment conveyor 256 and 258 as illustrated can comprise a frame structure 270, a plurality of rotatable pulleys 271 associated with the frame structure, and a continuous belt 272 carried on the pulleys. A drive system and conveyor shaft (not shown) can be used to rotatively drive one or more of the pulleys. The alignment conveyors 256 and 258 can comprise vacuum conveyors or other suitable transport devices.

The upper side panel positioning device 260 can comprise any suitable device for positioning the front side panels 34 and fastening components 84 and 85 for proper engagement with the back waist region 24. In the illustrated embodiment, the upper side panel positioning device 260 comprises a folding shoulder 280 and a mounting flange 282, which portions can be integrally formed or separate elements bonded together. The forming shoulder 280 can provide a gradual curvature to fold and invert the front side panels 34 as they travel from the position illustrated in FIG. 10 to the downstream position illustrated in FIG. 11. The illustrated forming shoulder 280 comprises a lip 284 adjacent the distal edge of the forming shoulder which lip is directed back toward the machine center line. The forming shoulder 280 can be formed of low friction materials or coatings such as those described above in relation to the separation plates 230. The size and position of the forming shoulder 280 will depend to some extent on the size of the side panels and the fastening components of the garment. The mounting flange 282 can be connected to the upper alignment conveyor 256 as illustrated or another suitable support structure. After the front side panels 34 have been folded, the second fastening components 84 and 85 are separated from one another by a post inversion distance which is less than the initial distance between the second fastening components.

One or both of the side panels 34 and 134 can be smoothed out or straightened if desired by various means including fluid stabilizing devices, such as air knives, air bars, air nozzles, vacuum means or the like. Such fluid stabilizing devices can be mounted on or in close proximity to the alignment conveyors 256 and 258 or to other suitable structures. In an alternative embodiment, the folding conveyors 206 and 208 and/or the alignment conveyors 256 and 258 can incorporate fluid stabilizing devices consisting of fluid manifolds operatively connected to a high pressure fluid source to fluidly shake the side panels. Suitable mechanisms for smoothing and straightening the side panels 34 and 134 are disclosed in U.S. Pat. No. 5,046,272 issued Sep. 10, 1991 to Vogt et al., which is incorporated herein by reference. The terms "air" and "fluid" are used interchangeably herein to refer to any gaseous substance, for example, air at ambient temperature. Where the specific application permits, the term "fluid" also includes any liquid medium.

Figure 12:
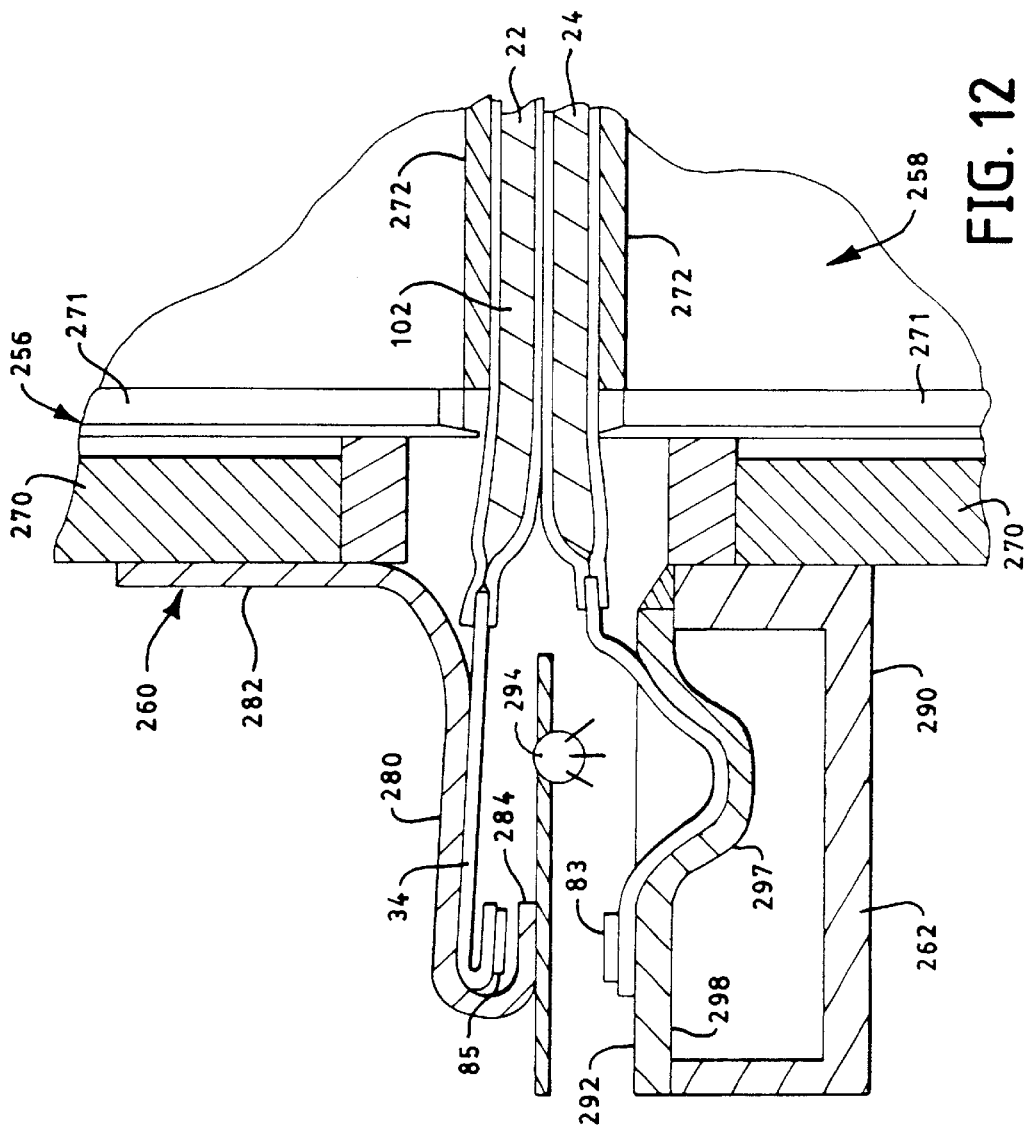

FIG. 12 illustrates the training pant 102 between the upper and lower alignment conveyors 256 and 258 at a location downstream of the location illustrated in FIG. 11. As illustrated in FIG. 12, the lower side panel positioning devices 262 can modify the contour of the back side panels 134 so that the first fastening components 82 and 83 are transversely displaced closer together, whereby the post displacement distance is less than the initial distance between the fastening components. The lower side panel positioning devices 262 can comprise any suitable devices for modifying the transverse position of the first fastening components 82 and 83. The illustrated side panel positioning devices 262 scrunch portions of the back waist region 24 to reduce the distance between the first fastening components 82 and 83. Specifically, the lower side panel positioning devices 262 can align the fastening components 82–85 for engagement by reducing the transverse distance between the first fastening components 82 and 83 so that the post displacement distance is less than the initial distance and is substantially equal to the post inversion distance between the second fastening components 84 and 85.

The illustrated lower side panel positioning devices 262 can comprise a frame structure 290 and a guide plate 292 disposed on the frame structure, or optionally can comprise only a guide plate. The guide plate 292 can have a contoured surface which can be generally flat near the upstream end (FIG. 11) and be contoured further downstream (FIG. 12). In particular, the guide plate 292 can define a recessed portion 297 and a support portion 298 transversely outward from the recessed portion relative to the machine center line. As the training pant 102 progresses in the machine direction 108 through the seaming section 250, the back side panels 134 can be drawn or forced against the guide plate 292. The illustrated embodiment includes a air bar, nozzle or the like 294 mounted on the separation plate 230 and operatively connected to a source of pressurized air (not shown). The air bar 294 can be positioned at a cross-machine direction location that corresponds to the recessed portion 297 such that expelled air from the air bar forces the back side panels 134 into the recessed portion. As the back side panels 134 are forced into the recessed portions 297, the first fastening components 82 and 83 are transversely displaced closer together to a post displacement distance. The guide plate 292 can be formed of low friction materials or coatings such as those described above in relation to the separation plates 230. The lip 284 of the folding shoulder 280, the separation plate 230 or other suitable structure or arrangement can be used to prevent premature engagement of the fastening components.

Figure 13:
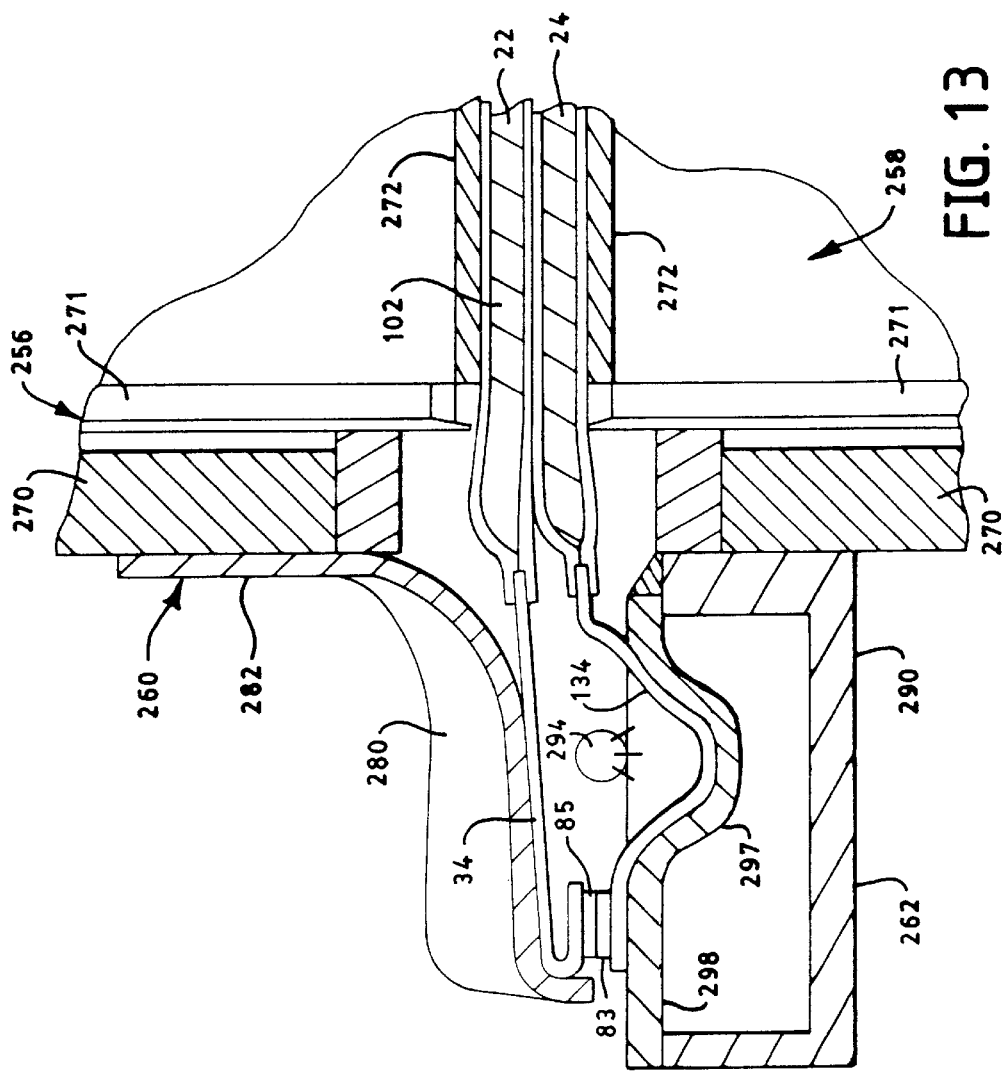

FIG. 13 illustrates the training pant 102 between the upper and lower alignment conveyors 256 and 258 at a location downstream of the location illustrated in FIG. 12. The fastening components 82–85 can be brought into contact with one another, for example, after passing the downstream end of the forming shoulder lip 284. Supplemental fastener engagement devices such as rollers, fluid blasts or the like can be used to more aggressively engage the fastening components. The air bar 294 can extend downstream past the end of the separation plate 230, as illustrated, where it can if desired continue to force the side panels 134 into the recessed portions 297 during fastener engagement.

Figure 14:
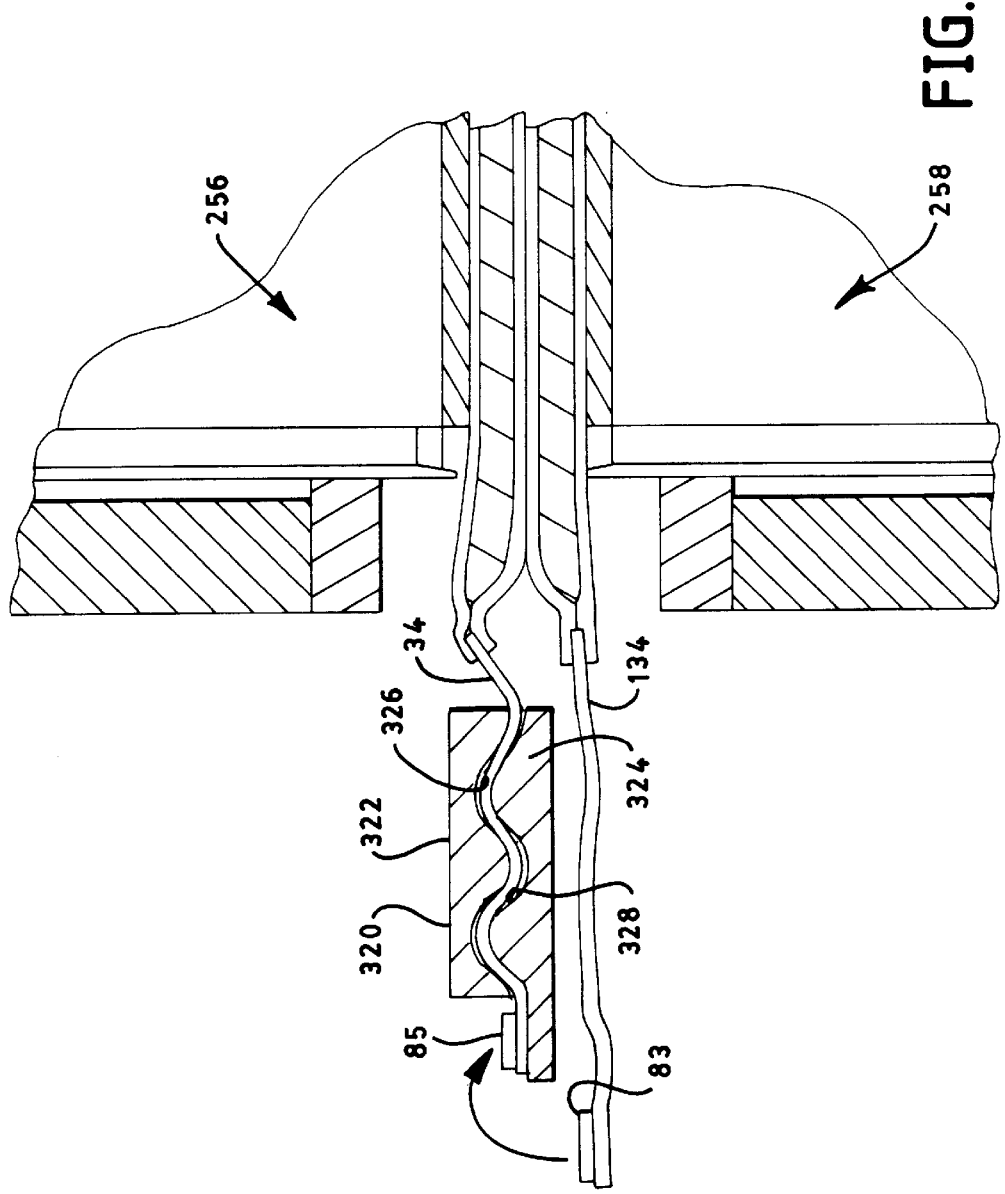
FIG. 14 illustrates an enlarged side view of a portion of a training pant operatively positioned with a side panel positioning device.

FIG. 14 illustrates an enlarged side view of a portion of a training pant in operable association with a side panel positioning device 320. The side panel positioning device 320 comprises contoured skid plates 322 and 324 having complementary shaped surfaces 326 and 328 respectively. A front side panel 34 is illustrated positioned between the shaped surfaces 326 and 328. The contouring or shaping of the front side panels 34 caused by the shaped surfaces 326 and 328 reduces the transverse distance between the second fastening components 84 and 85. The back side panels 134 can then be folded upward and inward in the direction of the arrow to engage the fastening components 83 and 85.

Figure 15:
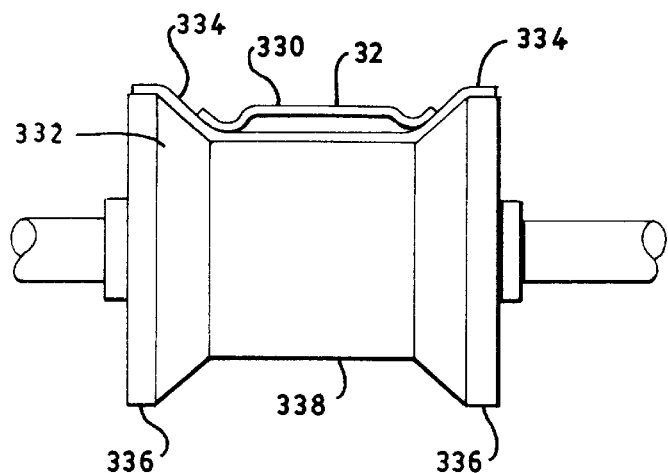
FIG. 15 illustrates an enlarged section view of one waist region of a training pant disposed on a contoured nip roll.

FIG. 15 illustrates an enlarged section view of one waist region of a training pant 330 disposed on a contoured nip roll 332. The training pant 330 comprises integral side panels 334 that can be refastenably engaged by mating fastening components on the opposite waist region (not shown). Thus, the side panels 334 define regions that function as fastening components. The contoured nip roll 332 as illustrated defines support portions 336 and a recessed portion 338 disposed between the support portions. The training pant 330 can be introduced onto the contoured nip roll 332, for example by a similarly contoured skid plate, so that the waist region assumes the shape of the contoured nip roll. Shaping the absorbent chassis 32 and/or side panels 334 on the contoured nip roll 332 reduces the transverse distance between the fastening components. An exemplary device comprising a contoured nip roll is disclosed in U.S. patent application Ser. No. 09/855,450, filed on May 15, 2001 by D. A. Maxton et al. and titled "Refastenable Bonding Of Garment Side Panels."

Figure 16:
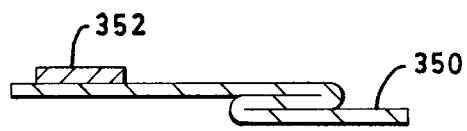
FIG. 16 illustrates an enlarged section view of a portion of a pant waist region during the manufacturing process, the waist region having been folded to transversely displace a fastening component.
Figure 17:
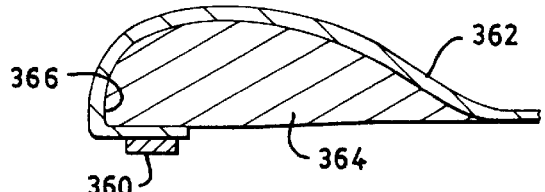
FIG. 17 illustrates another enlarged section view of a portion of a pant waist region during the manufacturing process, the waist region having a side panel moved over a contoured bar to invert and transversely displace a fastening component.

FIGS. 16 and 17 illustrate other variations for transversely displacing fastening components. In FIG. 16, a side panel 350 or other portion of a waist region can be folded so that the fastening component 352 is transversely displaced inward toward the machine center line and toward the other fastening component. The side panel or other portion can be folded with folding boards, vacuum devices or air nozzles without inverting the fastening component 352. In contrast, FIG. 17 illustrates a fastening component 360 that has been both inverted and transversely displaced. In this embodiment, the separate fastening component 360 is bonded to a distal region of a side panel 362. The side panel 362 can be moved in a machine direction onto a contoured bar 364 formed of a low friction material. The shape of the contoured bar 364 causes the fastening component 360 to be transversely displaced inward toward the machine center line and toward the other fastening component. In addition, the distal region of the side panel 362 can be motivated around a corner 366 of the contoured bar 364, for example using air blasts or air bars, such that the fastening component 360 is inverted.

Figure 18:
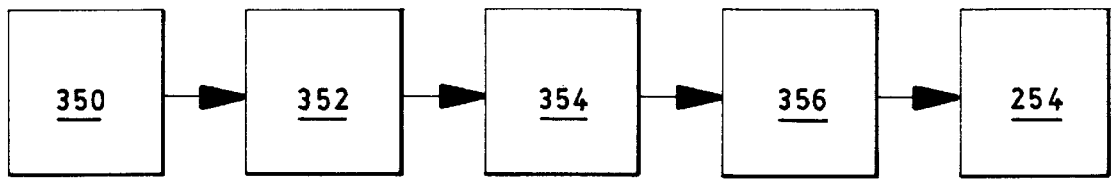
FIG. 18 schematically illustrates a flow diagram for manufacture of one embodiment of a pant according to the present invention.

FIG. 18 schematically illustrates a flow diagram for manufacture of one embodiment of pants according to the present invention. The components of the pants 20 can be provided and bonded together in an assembly section 350, typically in the form of a continuous web of interconnected and partially assembled pants. In particular embodiments, the pants 20 can comprise a material that is adapted to elongate or retract upon activation. Such activatable materials can be positioned in at least one of the waist regions and oriented such that the material elongates or retracts parallel to the transverse axis of the pant. The assembly section 350 can include a cutting mechanism which selectively cuts the web into discrete, partially assembled training pants. The discrete training pants 20 can then be folded in half at a folding section 352 using any suitable folding mechanism.

The training pants 20 can be transported to an activation section 354, which can but need not necessarily follow the folding section 352. The activation section 354 can comprise an activation source such as a heating unit to instigate elongation or retraction of the activatable material. Examples of activation sources that can be employed in the present process are disclosed in U.S. Pat. No. 4,640,726 issued Feb. 3, 1987 to Sallee et al. and U.S. Pat. No. 4,663,106 issued May 5, 1987 to Pomplun et al., which are incorporated herein by reference. In the illustrated embodiment, at least a portion of the activatable material is activated and caused to elongate or retract prior to engagement of the fastening components 82–85. By way of illustration, the waist elastic members 54 and 56, the side panels 34 and 134, and/or other components of the training pant can comprise activatable materials.

The elongation or retraction of the activatable material can transversely displace the fastening components 82–83 or 84–85 in one waist region to move either farther apart or closer together. Thus, the post displacement distance between the fastening components will be different than the initial distance between the fastening components. Specifically, it will be greater if the activatable material elongates upon activation and smaller if the activatable material retracts upon activation. The activation section 354 can comprise a separate stage of the manufacturing operation or can be incorporated into another stage. Activation can occur before, during or after folding.

The training pants 20 can next be transported to a seaming section 356, where the waist regions are joined to form refastenable seams 88. While the waist regions 22 and 24 can be positioned in an overlapping configuration for forming the lap seams before, during or after activation, the fastening components are desirably engaged after activation. After the fastening components are engaged, the training pants 20 can be processed through various finishing stations 254, including packaging operations to place a plurality of prefastened and refastenable pants in a sealed package.

Pants having a wide variety of configurations can be manufactured using the processes disclosed herein. Such configurations can include, among others, pants having the front and back waist regions of the same width, pants with one waist region wider than the other, pants with refastenable seams that are disposed at the sides of the wearer, pants with refastenable seams that are disposed forward or backward from the sides of the wearer, pants formed with fasteners initially on the same major surface, and pants formed with fasteners initially on opposite major surfaces. The processes disclosed herein can be adapted to accommodate any such pant configurations. For example, only one waist region can be inverted and/or transversely displaced, both waist regions can be inverted, transversely displaced, or both inverted and transversely displaced, or any other combination of inverting and/or transversely displacing one waist region and inverting and/or transversely displacing the other waist region. Moreover, a waist region that is wider, narrower, or the same width as the other waist region can be transversely displaced inward or outward, or inverted and transversely displaced inward or outward. A few of the many possibilities would include the following: simply transversely displacing inward or outward the fasteners in one waist region; in a pant with same width waist regions, inverting and transversely displacing outward the fasteners in one waist region; in a pant with one waist region narrower than the other, inverting the fasteners of the wider waist region and transversely displacing outward the fasteners of the narrower waist region; in a pant with one waist region narrower than the other, inverting the fasteners of the narrower waist region and transversely displacing inward the fasteners of the wider waist region; or the like.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A manufacturing process by a machine for making prefastened and refastenable pants, comprising:

providing a plurality of discrete articles, each article having first and second waist regions, a crotch region interconnecting the waist regions, first fastening components disposed in the first waist region and separated from one another by an initial distance, and second fastening components disposed in the second waist region and adapted to refastenably engage the first fastening components;

transporting the plurality of discrete articles in a machine direction via a transport system;

transversely displacing the first fastening components so that the first fastening components are separated from one another by a post displacement distance not equal to the initial distance; and engaging the first and second fastening components subsequent to transversely displacing the first fastening components and at a downstream machine direction location to form a plurality of prefastened and refastenable pants.

2. The process of claim 1, further comprising folding the first waist region to invert the first fastening components.

3. The process of claim 1, further comprising folding the second waist region to invert the second fastening components.

4. The process of claim 1, wherein the first and second fastening components are disposed on opposite major surfaces.

5. The process of claim 1, wherein the fastening components comprise separate elements bonded to side panels of the waist regions.

6. The process of claim 1, wherein the first waist region comprises opposite side panels and the fastening components comprise integral portions of the side panels.

7. The process of claim 1, wherein the distance between the first fastening components is changed without inverting the first fastening components.

8. The process of claim 1, wherein the post displacement distance is less than the initial distance.

9. The process of claim 8, wherein transversely displacing the first fastening components is selected from gathering, scrunching, folding, pleating, corrugating, wrinkling, contracting, necking, contouring, shaping, bowing, separating, and elevating portions of the first waist region.

10. The process of claim 8, wherein transversely displacing the first fastening components comprises gathering portions of the first waist region around a device selected from a bar, rod, tube, and plate.

11. The process of claim 8, wherein transversely displacing the first fastening components comprises gathering portions of the first waist region in a channel.

12. The process of claim 8, wherein transversely displacing the first fastening components comprises gathering portions of the first waist region that are disposed between the fastening components.

13. The process of claim 12, wherein the gathered portions of the first waist region comprise an absorbent chassis.

14. The process of claim 12, wherein the gathered portions of the first waist region comprise side panels.

15. The process of claim 12, wherein the gathered portions of the first waist region comprise portions of the first fastening components.

16. The process of claim 8, wherein transversely displacing the first fastening components comprises creating an elevation difference between portions of the first waist region containing the first fastening components and another portion of the first waist region.

17. The process of claim 8, wherein the first waist region comprises an absorbent chassis and opposite side panels, the fastening components are disposed on the side panels, and the absorbent chassis and side panels are repositioned relative to one another to create an elevation difference between at least a portion of the absorbent chassis and the side panels.

18. The process of claim 8, wherein transversely displacing the first fastening components comprises transversely contracting the first waist region.

19. The process of claim 18, wherein the pant comprises an activatable retractive material that is adapted to contract in a direction generally perpendicular to a longitudinal center line.

20. The process of claim 1, wherein the post displacement distance is greater than the initial distance.

21. The process of claim 20, wherein transversely displacing the first fastening components comprises altering the structure of a material within the first waist region.

22. The process of claim 21, wherein the pant comprises an activatable material that is adapted to elongate in a direction generally perpendicular to a longitudinal center line.

23. The process of claim 20, wherein transversely displacing the first fastening components comprises transversely stretching a material within the first waist region.

24. A process for making prefastened and refastenable pants, comprising:
providing a plurality of discrete articles, each article having first and second waist regions, a crotch region interconnecting the waist regions, first fastening components disposed in the first waist region and separated from one another by an initial distance, and second fastening components disposed in the second waist region and adapted to refastenable engage the first fastening components;
transversely displacing the first fastening components so that the first fastening components are separated from one another by a post displacement distance not equal to the initial distance; and
engaging the first and second fastening components subsequent to transversely displacing the first fastening components to form a plurality of prefastened and refastenable pants;
wherein the post displacement distance is less than the initial distance; and
wherein transversely displacing the first fastening components comprises modifying the contour of the pant using a device selected from a vacuum device, contoured drum, contoured roll, pressurized air nozzles, converging conveyors, chains, vertical vacuum belts, and cam systems.

25. A process for making prefastened and refastenable pants, comprising:
providing a plurality of discrete articles, each article having first and second waist regions, a crotch region interconnecting the waist regions, first fastening components disposed in the first waist region and separated from one another by an initial distance, and second fastening components disposed in the second waist region and adapted to refastenable engage the first fastening components;
transversely displacing the first fastening components so that the first fastening components are separated from one another by a post displacement distance not equal to the initial distance; and
engaging the first and second fastening components subsequent to transversely displacing the first fastening components to form a plurality of prefastened and refastenable pants;
wherein the post displacement distance is less than the initial distance;
wherein the first waist region comprises an absorbent chassis and opposite side panels, the fastening components are disposed on the side panels, and the absorbent chassis and side panels are repositioned relative to one another to create an elevation difference between at least a portion of the absorbent chassis and the side panels; and
wherein creating an elevation difference comprises using a device selected from a contoured roll, a multi-path conveyor, guiding surfaces, and fluid positioning devices.

26. A process for making prefastened and refastenable pants, comprising:

providing a plurality of discrete articles, each article having first and second waist regions, a crotch region interconnecting the waist regions, first fastening components disposed in the first waist region and separated from one another by an initial distance, and second fastening components disposed in the second waist region and adapted to refastenable engage the first fastening components;

transversely displacing the first fastening components so that the first fastening components are separated from one another by a post displacement distance not equal to the initial distance; and engaging the first and second fastening components subsequent to transversely displacing the first fastening components to form a plurality of prefastened and refastenable pants;

wherein the post displacement distance is greater than the initial distance; and wherein transversely displacing the first fastening components comprises increasing the distance between the first fastening components using a device selected from a tenter frame, diverging conveyors, and angled nip rolls.

27. A manufacturing process by a machine for making prefastened and refastenable pants, comprising:

providing a plurality of discrete articles, each article having first and second waist regions, a crotch region interconnecting the waist regions, opposite first and second major surfaces, opposite side panels in each of the waist regions, first fastening components disposed on the first surface of the side panels in the first waist region and separated from one another by an initial distance, and second fastening components disposed on the second surface of the side panels in the second waist region and adapted to refastenably engage the first fastening components;

transporting the plurality of discrete articles in a machine direction via a transport system;

modifying the side panels in the second waist region to invert the second fastening components, the second fastening components after modification being spaced apart by a post inversion distance;

transversely displacing the first fastening components so that the first fastening components are separated from one another by a post displacement distance not equal to the initial distance and substantially equal to the post inversion distance; and engaging the first and second fastening components, subsequent to transversely displacing the first fastening components and inverting the second fastening components, at a downstream machine direction location to form a plurality of prefastened and refastenable pants.

28. The process of claim 27, wherein the initial distance between the first fastening components is substantially equal to an initial distance between the second fastening components prior to modifying the side panels in the second waist region.

29. The process of claim 27, wherein the distance between the first fastening components is changed without inverting the first fastening components.

30. The process of claim 27, wherein the post displacement distance is less than the initial distance.

31. The process of claim 27, wherein transversely displacing the first fastening components is selected from gathering, scrunching, folding, pleating, corrugating, wrinkling, contracting, necking, contouring, shaping, bowing, separating, and elevating portions of the first waist region.

32. The process of claim 27, wherein transversely displacing the first fastening components comprises creating an elevation difference between portions of the first waist region containing the first fastening components and another portion of the first waist region.

33. The process of claim 27, wherein the post displacement distance is greater than the initial distance.

34. A manufacturing process by a machine for making prefastened and refastenable pants, comprising:

providing a plurality of discrete articles, each article having first and second waist regions of the same width, a crotch region interconnecting the waist regions, opposite first and second major surfaces, opposite side panels in each of the waist regions, first fastening components disposed on the first surface of the side panels in the first waist region and separated from one another by an initial distance, and second fastening components disposed on the second surface of the side panels in the second waist region and separated from one another by substantially the same initial distance, the first and second fastening components adapted to refastenably engage one another;

transporting the plurality of discrete articles in a machine direction via a transport system;

modifying the side panels in the second waist region to invert the second fastening components, the second fastening components after modification being spaced apart by a post inversion distance less than the initial distance;

transversely displacing the first fastening components so that the first fastening components are separated from one another by a post displacement distance less than the initial distance and substantially equal to the post inversion distance;

engaging the first and second fastening components subsequent to transversely displacing the first fastening components and inverting the second fastening components, at a downstream machine direction location to form a plurality of prefastened and refastenable pants, and packaging the plurality of prefastened and refastenable pants in a sealed package.

* * * * *